United States Patent [19]

Nishimoto et al.

[11] Patent Number: 5,538,883
[45] Date of Patent: Jul. 23, 1996

[54] MALTOSE-TREHALOSE CONVERTING ENZYME

[75] Inventors: Tomoyuki Nishimoto; Hiroto Chaen; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 277,007

[22] Filed: Jul. 19, 1994

[30] Foreign Application Priority Data

Jul. 20, 1993 [JP] Japan .................................. 5-199971
Jun. 3, 1994 [JP] Japan .................................. 6-144092

[51] Int. Cl.$^6$ .................................................. C12N 9/24
[52] U.S. Cl. .................... 435/200; 435/253.3; 435/252.1
[58] Field of Search ............................... 435/200, 253.3, 435/252.1

[56] References Cited

U.S. PATENT DOCUMENTS

| | | | |
|---|---|---|---|
| 3,795,584 | 3/1974 | Mitsuhashi et al. | 435/95 |
| 3,832,285 | 8/1974 | Kurimoto | 435/95 |
| 4,032,403 | 6/1977 | Sakai et al. | 435/95 |
| 4,521,252 | 6/1985 | Miyake et al. | 127/46.3 |
| 4,594,322 | 6/1986 | Thompson et al. | 435/95 |
| 5,169,767 | 12/1992 | Matsuura et al. | 435/100 |

FOREIGN PATENT DOCUMENTS

| | | |
|---|---|---|
| 257535 | 3/1988 | European Pat. Off. . |
| 302838 | 2/1989 | European Pat. Off. . |
| 327391 | 8/1989 | European Pat. Off. . |
| 447125 | 9/1991 | European Pat. Off. . |
| 606753 | 7/1994 | European Pat. Off. . |
| 1958014 | 6/1970 | Germany . |
| 47-013089 | 4/1972 | Japan . |
| 50-154485 | 12/1975 | Japan . |
| 54-003938 | 2/1979 | Japan . |
| 56-011437 | 3/1981 | Japan . |
| 56-017078 | 4/1981 | Japan . |
| 56-028154 | 6/1981 | Japan . |
| 56-028153 | 6/1981 | Japan . |
| 57-003356 | 1/1982 | Japan . |
| 58-023799 | 2/1983 | Japan . |
| 58-072598 | 4/1983 | Japan . |
| 58-216695 | 12/1983 | Japan . |
| 63-042696 | 2/1988 | Japan . |
| 01034296 | 2/1989 | Japan . |
| 4-281795 | 10/1992 | Japan . |
| 2106912 | 4/1983 | United Kingdom . |
| WO91/17255 | 11/1991 | WIPO . |
| WO92/03565 | 3/1992 | WIPO . |

OTHER PUBLICATIONS

Schick et al–Proceedings of the Int'l Symposium on Biochemistry Engineering, 1990, 126–9.

Murao et al., Agric. Biol. Chem., 49(7), 2113–2118, 1985.

Toussaint et al., Biotechnology Letters, vol. 12 (8), 587–592, 1990.

Suzuki et al; Pimelobacter Gen. Nov., A New Genus Of coryneform Bacteria With LL–Diaminopimelic Acid In The Cell Wall, Journal of General Applied Microbiology; vol. 29, pp. 59–71, 1983.

Krieg et al; *Bergey's Manual Of Systematic Bacteriology;* vol. 1, pp. 187–199, 1984.

Krieg et al; *Bergey's Manual of Systematic Bacteriology;* vol. 2, pp. 1265, 1292, 1300, & 1482–1485; 1986.

Wolfrom et al; *Advances in Carbohydrate Chemistry*, vol. 18, pp. 201–225, 1963.

Hoelzle et al; *Increased Accumulation of Trehalose in Rhizobia cultured Under 1% Oxygen,* Applied and Environment Microbiology; vol. 56, No. 10, pp. 3213–3215; Oct., 1990.

Ikeda et al., Biotechnol. & Bioengineer., vol. 42, pp. 788–91, 1993.

Rastall et al., Biotech. Lett., vol. 14, No. 5, 373–78, 1992.

*Primary Examiner*—David M. Naff
*Assistant Examiner*—Jean C. Witz
*Attorney, Agent, or Firm*—Browdy and Neimark

[57] ABSTRACT

An enzyme, which has a molecular weight of about 57,000–120,000 daltons on SDS-PAGE and a pI of about 3.8–5.1 on isoelectrophoresis using ampholyte, converts maltose into trehalose and vice versa. The enzyme was isolated from microorganisms of the genera Pimelobacter, Pseudomonas and Thermus. By using the enzyme, trehalose is readily formed from a commercially available maltose in an industrial scale and a relatively-low cost. Trehalose and saccharide compositions containing the same, which are preparable with the enzyme, are suitably used in food products, cosmetic compositions and pharmaceutical compositions.

4 Claims, 12 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 10 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Gly Lys Trp Pro Arg Ala Ala Phe Ile Asp
    1               5                   10

(2) INFORMATION FOR SEQ ID NO:2:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Ser Thr Val Leu Gly Glu Glu Pro Glu Trp Phe Arg Thr Ala Val Phe
    1               5                   10                  15
    Tyr Glu (2) INFORMATION FOR SEQ ID NO:3:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Met Asp Pro Leu Trp Tyr Lys Asp Ala Val Ile Tyr Gln
    1               5                   10

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 2
            (D) OTHER INFORMATION: /note="Xaa =Phe or Pro"

(ix) FEATURE:
            (A) NAME/KEY: Peptide
            (B) LOCATION: 4
            (D) OTHER INFORMATION: /note="Xaa =Thr or Pro"

(ix) FEATURE:
            (A) NAME/KEY: Peptide
            (B) LOCATION: 6
            (D) OTHER INFORMATION: /note="Xaa =Val or Ala"

(xi) SEQUENCE DESCRIPTION: SEQ ID NO:4:

Trp Xaa Arg Xaa Ala Xaa Phe
    1               5

(2) INFORMATION FOR SEQ ID NO:5:

(i) SEQUENCE CHARACTERISTICS:

( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3
        ( D ) OTHER INFORMATION: /note="Xaa =Phe or Ile"

( x i ) SEQUENCE DESCRIPTION: SEQ ID NO:5:

Ala Val Xaa Tyr
1

MALTOSE-TREHALOSE CONVERTING ENZYME

BACKGROUND OF THE INVENTION

1. Field of the Invention

The present invention relates to a novel enzyme, and preparation and uses thereof. More particularly, the present invention relates to an enzyme which converts maltose into trehalose or converts trehalose into maltose (hereinafter designated as "maltose-trehalose converting enzyme"), as well as to preparation thereof. The present invention further relates to a microorganism capable of producing the enzyme, trehalose prepared with the enzyme, saccharide compositions containing the trehalose, and compositions containing the trehalose or the saccharide composition.

2. Description of the Prior Art

Trehalose or α, α-trehalose has been known as a non-reducing saccharide consisting of glucoses. As is described in *Advances in Carbohydrate Chemistry*, Vol.18, pp.201–225 (1963), published by Academic Press, USA, and *Applied and Environmental Microbiology*, Vol.56, pp.3, 213–3,215 (1990), trehalose widely exists in microorganisms, mushrooms, insects, etc., though the content is relatively low. Trehalose is a non-reducing saccharide, so that it neither reacts with substances containing amino groups such as amino acids and proteins, induces the amino-carbonyl reaction, nor deteriorates amino acid-containing substances. Thus, trehalose can be used without a fear of causing an unsatisfactory browning and deterioration. Because of these, the establishment of an industrial-scale preparation of trehalose has been in great demand.

Conventional preparations of trehalose are, for example, those disclosed in Japanese Patent Laid-Open No.154,485/75 wherein microorganisms are utilized, and in Japanese Patent Laid-Open No.216,695/83 wherein maltose is converted into trehalose by the combination use of maltose- and trehalose-phosphorylases. The former, however, is not suitable for the industrial-scale preparation because the content of trehalose present in microorganisms as a starting material is usually lower than 15 w/w % (the wording "w/w %" is abbreviated as "%" in the specification, unless otherwise specified), on a dry solid basis (d.s.b.), and the extraction and purification steps are complicated. The latter has the following demerits: (i) Since trehalose is formed via glucose-1-phosphate, the concentration of maltose as a substrate could not be set to a satisfactorily high-level; (ii) the enzymatic reaction systems of the phosphorylases are reversible reactions, and their yields of the objective trehalose are relatively low; and (iii) it is substantially difficult to retain their reaction systems stably and to proceed their enzymatic reactions smoothly. Therefore, the aforesaid conventional preparations could not be used as an industrial-scale preparation.

It is known that partial starch hydrolysates, prepared from a material starch such as liquefied starch, dextrins and maltooligosaccharides, usually exhibit a reducing power because of their reducing end groups. The reducing power is generally expressed by "Dextrose Equivalent (DE) value" based on the dry weight. It is known that among reducing partial starch hydrolysates, those with a relatively-high DE value generally have a considerably-low molecular weight and viscosity, as well as a relatively-high level of sweetness and reactivity, and readily react with substances having amino groups such as amino acids and proteins to cause an unsatisfactory browning, smell and deterioration of their quality. Since the properties of reducing partial starch hydrolysates are varied dependently on their DE values, the relationship between reducing partial starch hydrolysates and their DE values is significant. It has been even believed impossible to break away the relationship in this field.

As regards the preparation of trehalose, it is reported in the column titled "Oligosaccharides" in the chapter of "Current Status of Starch Application Development and Related Problems" in *"Food Chemicals"*, No.88, pp.67–72 (August, 1992) that "In spite of a wide applicability of trehalose, the enzymatic preparation via a direct saccharide-transfer reaction or a hydrolytic reaction has been reported to be scientifically almost impossible in this field." Thus, the preparation of trehalose by an enzymatic reaction using starch as a material has been deemed scientifically very difficult.

The present inventors, however, had changed this common sense and succeeded to establish a preparation of trehalose as disclosed in Japanese Patent Application No.362,131/92 wherein trehalose is directly produced from non-reducing partial starch hydrolysates by allowing glucoamylase together with a non-reducing saccharide-forming enzyme capable of forming non-reducing saccharides, having a trehalose structure as an end unit and having a degree of glucose polymerization of 3 or higher, to act on reducing partial starch hydrolysates having a degree of glucose polymerization of 3 or higher, prepared from a material starch. The method, however, requires 2 or more types of enzymes and employs as a material a relatively-high molecular weight amylaceous saccharide having a degree of glucose polymerization of 3 or higher as well as a relatively-high viscosity. In addition, the saccharide composition of the resultant product is considerably complicated, and this may result in a high production cost. Therefore, the establishment of a novel preparation of trehalose in which trehalose is formed from maltose and partial starch hydrolysates having a degree of glucose polymerization of 2, both of which are industrially produced, stably supplied and commercially available.

SUMMARY OF THE INVENTION

It is an object of the present invention to provide a maltose-trehalose converting enzyme which converts an industrially producible and stably suppliable maltose into trehalose and to provide a novel preparation and uses of trehalose and a saccharide composition containing the trehalose prepared with the enzyme.

In order to attain the object, the present inventors have extensively screened microorganisms capable of producing a novel saccharide-converting enzyme which forms trehalose from maltose. As a result, we found that a microorganism of the genus Pimelobacter, i.e. Pimelobacter sp. R48, isolated from a soil in Okayama-city, Okayama, Japan; a microorganism of the genus Pseudomonas, i.e. *Pseudomonas putida* H262, isolated from a soil in Nishinomiya-city, Hyogo, Japan; and a microorganism of the genus Thermus form a novel maltose-trehalose converting enzyme which converts maltose into trehalose, and established a preparation of trehalose and a saccharide composition containing the trehalose, as well as compositions such as food products, cosmetics and pharmaceuticals containing the trehalose or the saccharide composition. Thus, we accomplished this invention.

BRIEF DESCRIPTION ACCOMPANYING DRAWINGS

DETAILED DESCRIPTION OF THE INVENTION

Figure 1:
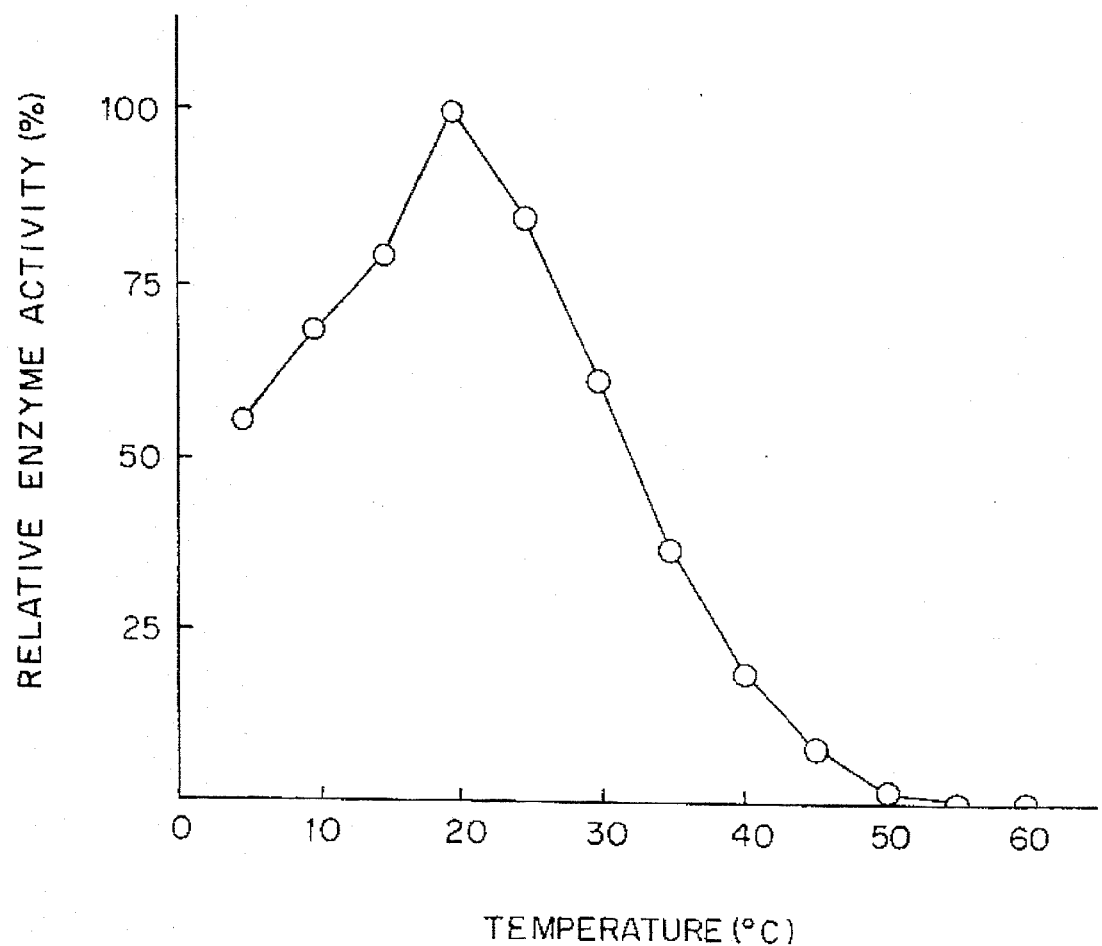
FIG. 1 shows the influence of temperature on the enzyme activity of the present maltose-trehalose converting enzyme derived from Pimelobacter sp. R48.

The present invention relates to a maltose-trehalose converting enzyme, and preparation and uses thereof. More particularly, the present invention relates to a novel maltose-trehalose converting enzyme which converts maltose into trehalose or converts trehalose into maltose, as well as to preparation thereof. The present invention further relates to a microorganism capable of producing the enzyme, a trehalose prepared with the enzyme, a saccharide composition containing the trehalose, and a composition containing the trehalose or the saccharide composition.

The identification test of a microorganism of the genus Pimelobacter, i.e. "Pimelobacter sp. R48", and a microorganism of the genus Pseudomonas, i.e. *Pseudomonas putida* H262, according to the present invention gave the following results. The test was conducted in accordance with the method as described in "Biseibutsu-no-Bunrui-to-Dotei" (Classification and Identification of Microorganisms), edited by Takeji Hasegawa, published by Japan Scientific Societies Press, Tokyo, Japan (1985).

The results of Pimelobacter sp. R48 were as follows:
A. Morphology
  (1) Characteristics of cells when incubated at 27° C. in nutrient agar
  Usually existing in a rod form of 0.5–0.9×1.5–4.0 μm;
  Existing single but uncommonly existing in a V-form pair or in a linked form;
  Possessing no motility and being asporogenic;
  Non acid-fast; and
  Gram stain: Positive.
  (2) Characteristics of cells when incubated at 27° C. in agar medium supplemented with yeast- and malto-extracts
  Having a size of 0.6–1.0×1.3–4.2 μm after one-day culture and existing in the form of a nearly cocci with a size of 0.6–1.0×1.0–2.5 μm after 3-day culture;
  Exhibiting polymorphism; and
  Existing single but uncommonly existing in a V-form pair or in a linked form.
B. Cultural property
  (1) Characteristics of colony formed when incubated at 27° C. in nutrient agar plate
  Shape: Circular colony having a diameter of 0.5 mm after 24-hours incubation and 1.5–2 mm after 3-days incubation;
  Rim: Auriculate-like;
  Projection: Hemispherical shape;
  Gloss: None;
  Surface: Rugose-like;
  Color: Creamy and opaque colony;
  (2) Characteristics of colony formed when incubated at 27° C. in agar plate supplemented with yeast- and malto-extracts
  Shape: Circular colony having a diameter of about 1–1.5 mm after 3-days incubation;
  Rim: Auriculate-like;
  Projection: Hemispherical shape;
  Gloss: None;
  Surface: Rugose-like;
  Color: Creamy and opaque colony;
  (3) Characteristics of colony formed when incubated at 27° C. in slant nutrient agar
  Growth: Satisfactory;
  Shape: Thread-like; and
  (4) Not liquefying gelatin when stab-cultured at 27° C. in nutrient gelatin.
C. Physiological properties
  (1) Reduction of nitrate: Positive;
  (2) Denitrification reaction: Negative;
  (3) Methyl red test: Negative;
  (4) VP-test: Negative;
  (5) Formation of indole: Negative;
  (6) Formation of hydrogen sulfide: Positive;
  (7) Hydrolysis of starch: Negative;
  (8) Utilization of citric acid: Positive;
  (9) Utilization of inorganic nitrogen source: Utilizing ammonium salts and nitrates;
  (10) Formation of pigment: Negative;
  (11) Urease: Negative;
  (12) Oxidase: Negative;
  (13) Catalase: Negative;
  (14) Growth conditions: Growing at a pH in the range of 5–9 and a temperature in the range of 15°–40° C.;
  (15) Oxygen requirements: Aerobic;

(16) Utilization of carbon source and acid formation

| Carbon source | Utilization | Acid formation |
|---|---|---|
| D-Glucose | + | − |
| D-Galactose | − | − |
| D-Fructose | + | − |
| D-Mannose | + | − |
| L-Arabinose | + | − |
| D-Xylose | + | − |
| L-Rhamnose | + | − |
| Maltose | + | − |
| Sucrose | + | − |
| Lactose | − | − |
| Trehalose | + | − |
| Raffinose | + | − |
| Mannitol | − | − |
| Dextrin | + | − |
| Dulcitol | − | − |

(17) Decarboxylase test on amino acid Negative against L-lysine, L-arginine and L-ornithine;

(18) Utilization of amino acid Utilizing sodium L-glutamate and sodium L-asparate;

(19) DNase: Negative;

(20) Formation of 3-ketolactose: Negative;

(21) Mol % guanine (G) plus cytosine (C) of DNA: 72%; and

(22) Main diamino acid of cell wall LL-Diaminopimelic acid.

The results of *Pseudomonas putida* H262 were as follows:

A. Morphology (1) Characteristics of cells when incubated at 27° C. in nutrient agar Usually existing in a rod form of 0.5–0.7×1.0–2.0 μm and possessing asporogenicity;

Possessing motility by flagellum;

Non acid-fast; and

Gram stain: Negative.

(2) Characteristics of cells when incubated at 27° C. in agar medium supplemented with yeast- and malto-extracts Having a size of 0.6–0.8×2.0–4.0 μm after one-day culture.

B. Cultural property (1) Characteristics of colony formed when incubated at 27° C. in nutrient agar plate Shape : Circular colony having a diameter of 1–2 mm after 24-hours incubation and 3.5–4 mm after 3-days incubation;

Rim: Entire;

Projection: Hemispherical shape;

Gloss: Moist gloss;

Surface: Smooth;

Color: Creamy or white opaque colony;

(2) Characteristics of colony formed when incubated at 27° C. in agar plate supplemented with yeast- and malto-extracts Shape Circular colony having a diameter of about 4–5 mm after 3-days incubation;

Rim: Entire;

Projection: Hemispherical shape;

Gloss: Moist gloss;

Surface: Smooth;

Color: Creamy or white opaque colony;

(3) Characteristics of colony formed when incubated at 27° C. in slant nutrient agar Growth : Satisfactory;

Shape : Thread-like. Forming a relatively-thin projection with a smooth surface, moist gloss, opaque and yellowish cream; and (4) Not liquefying gelatin when stab-cultured at 27° C. in nutrient gelatin.

C. Physiological properties (1) Reduction of nitrate in a succinic acid medium: Positive;

(2) Denitrification reaction: Negative;

(3) Methyl red test: Negative;

(4) VP-test: Negative;

(5) Formation of indole: Negative;

(6) Formation of hydrogen sulfide: Negative;

(7) Hydrolysis of starch: Negative;

(8) Accumulation of poly-β-hydroxybutylate: Negative (9) Decomposition of procatechuate: Orth-type

(10) Utilization of citric acid: Positive;

(11) Utilization of inorganic nitrogen source: Utilizing ammonium salts and nitrates;

(12) Formation of pigment: Pale yellowish pigment;

(13) Formation of fluorescent pigment: Positive

(14) Urease: Positive;

(15) Oxidase: Positive;

(16) Catalase: Positive;

(17) Growth conditions: Growing at a pH in the range of 5–9 and a temperature in the range of 10°–37° C.;

(18) Oxygen requirements: Aerobic;

(19) Utilization of carbon source and acid formation

| Carbon source | Utilization | Acid formation ability |
|---|---|---|
| D-Glucose | + | − |
| D-Galactose | − | − |
| D-Mannose | + | + |
| D-Fructose | + | − |
| L-Arabinose | + | − |
| D-Xylose | + | − |
| L-Rhamnose | + | − |
| Maltose | + | − |
| Sucrose | + | − |
| Lactose | − | − |
| Trehalose | + | − |
| Raffinose | + | − |
| Mannitol | − | − |
| Sorbitol | − | − |
| Dulcitol | − | − |
| Glycerol | + | + |

(20) Decarboxylase test on amino acid Negative against L-lysine and L-ornithine and positive against L-arginine;

(21) Utilization of amino acid Utilizing sodium L-glutamate, sodium L-asparate, sodium L-arginine, L-histidine, L-valine and D-alanine, but not L-tryptophane;

(22) DNase: Negative;

(23) Formation of 3-ketolactose: Negative; and

(24) Mol % guanine (G) plus cytosine (C) of DNA: 63%.

Based on the results, the bacteriological properties were compared with those of known microorganisms with reference to *Bergey's Manual of Systematic Bacteriology*, 1st edition (1984). As a result, it was revealed that the microorganism was identified as a microorganism of the species *Pseudomonas putida.*

The present inventors had named this microorganism "*Pseudomonas putida* H262", and deposited it on Feb. 23 1994, in National Institute of Bioscience and Human-Technology Agency of Industrial Science and Technology, Ibaraki, Japan. The deposition of the microorganism was accepted on the same day and has been maintained by the institute under the accession number of FERM BP-4579.

In addition to the above-identified microorganism, other strains of the genus Pseudomonas and their mutants can be adequately used in the invention as long as they produce the present maltose-trehalose converting enzyme.

Furthermore, microorganisms of the genus Thermus, for example, those of the species *Thermus aquaticus* (ATCC 25104), *Thermus aquaticus* (ATCC 33923), *Thermus filiformis* (ATCC 43280), *Thermus ruber* (ATCC 35948), Thermus sp. (ATCC 43814), and Thermus sp. (ATCC 43815) can be suitably used in the invention.

Any nutrient culture medium can be used in the invention as long as the microorganisms can grow therein and produce the present enzyme: For example, synthetic- and natural-nutrient culture media can be arbitrarily used. Any carbon-containing substance can be used in the invention as a carbon source as long as it is utilized by the microorganisms: Examples of such a carbon source are saccharides such as glucose, fructose, molasses, trehalose, lactose, sucrose, mannitol, sorbitol, partial starch hydrolysates; and organic acids such as citric acid and succinic acid as well as their salts. The concentrations of these carbon sources in nutrient culture media are appropriately chosen. For example, in the case of using glucose, a preferable concentration is usually 40 w/v % or lower, preferably, 10 w/v % or lower, d.s.b., in view of the growth and proliferation of the microorganisms. The nitrogen sources usable in the invention are, for example, inorganic nitrogen compounds such as ammonium salts and nitrates; and organic nitrogen-containing compounds such as urea, corn steep liquor, casein, peptone, yeast extract and meat extract. The inorganic ingredients usable in the invention are, for example, calcium salts, magnesium salts, potassium salts, sodium salts, phosphates and other salts of manganese, zinc, iron, copper, molybdenum and cobalt.

The cultural conditions used in the invention are those in which the microorganisms can grow and produce the present enzyme, for example, aerobic conditions at a temperature in the range of about 4°–80° C., preferably, a temperature in the range of about 20°–75° C.; and at a pH in the range of about 5–9, preferably, a pH in the range of 6–8.5. The cultivation time suitably used in the invention is set to a time longer than that required for the growth initiation of the microorganisms, preferably, 10–100 hours. The concentration of dissolved oxygen (DO) in nutrient culture media is not specifically restricted, and, usually a DO in the range of about 0.5–20 ppm is satisfactory. The DO level can be kept within the range by controlling the aeration rate, stirring nutrient culture media, supplementing oxygen to aeration, and increasing the inner pressure of fermenters. The culture can be carried out batchwise or in continuous manner.

After completion of the culture, the present enzyme is recovered therefrom. Inasmuch as the activity of the present enzyme is found in both cells and cell-free supernatants, they can be recovered and used as a crude enzyme. The resultant culture can be used intact as a crude enzyme. Conventional liquid-solid separation methods can be employed in the invention to remove cells from the culture. For example, methods to directly centrifuge the resultant culture and those to filtrate cells with precoat filters or to filtrate cells by the addition of filter aids, as well as to separate cells by membrane filtration using plate filters or hollow fibers, can be suitably used. Cell-free filtrates thus obtained can be used intact as an enzyme solution or may be concentrated in usual manner prior to their use. The concentration methods usable in the invention are, for example, salting out using ammonium sulfate, sedimentation using acetone and alcohol, and membrane filtration using plate filters, hollow fibers, etc.

In case of the present enzyme is an intracellular enzyme, it can be extracted from cells by conventional techniques, and the resultant extract can be used as a crude enzyme. In order to obtain such an extract, cells are disrupted by an ultrasonic disruption, mechanical disruption using glass beads or alumina, french-press disruption, etc., followed by subjecting the resultant to centrifugation or membrane filtration to obtain a clear crude-enzyme-solution.

Cell-free filtrates and their concentrates as well as cell extracts can be immobilized by conventional techniques. Examples of such an immobilization technique are conjugation methods using ion-exchangers, covalent linkages and absorptions using resins and membranes, and inclusion methods using high-molecular weight substances. Intact cells separated from the resultant culture can be used as a crude enzyme or may be immobilized prior to their use. For example, the cells are immobilized by mixing them with sodium alginate, and dropping the suspension in calcium chloride solution to gelatinize the drops into granules. The resultant granules can be fixed by polyethylene imine or glutaraldehyde prior to their use.

The crude enzyme solutions thus obtained can be used intact or purified by conventional methods prior to their use. For example, a purified enzyme preparation, which exhibits an electrophoretically single band, can be prepared by dialyzing a crude enzyme preparation, which had been prepared by salting out an extract from disrupted cells with ammonium sulfate and concentrating the resultant, and successively purifying the dialyzed solution on anion-exchange column chromatography using "DEAE-TOYOPEARL®", an anion exchanger; hydrophobic column chromatography using "BUTYL-TOYOPEARL®", a hydrophobic resin, all of which are products of Tosoh Corporation, Tokyo, Japan; anion-exchange column chromatography using "MONO Q HR5/5", an anion exchanger commercialized by Pharmacia LKB Biotechnology AB, Uppsala, Sweden; and gel filtration column chromatography using "TOYOPEARL®HW-55", a resin commercialized by Tosoh Corporation, Tokyo, Japan. These procedures provide an enzyme which shows an electrophoretically single band.

The present maltose-trehalose converting enzyme thus obtained has the following physicochemical properties:

(1) Action Converting maltose into trehalose and vice versa.

(2) Molecular weight About 57,000–120,000 daltons on sodium dodecylsulfate polyacrylamide gel electrophoresis (SDS-PAGE);

(3) Isoelectric point (pI) About 3.8–5.1 on isoelectrophoresis using ampholyte;

(4) Inhibition of activity Being inhibited by one mM $Cu^{++}$, $Hg^{++}$ and Tris-HCl buffer; and (5) Origin Originated from microorganisms.

More particularly, the physicochemical property of the present enzyme differs dependently on its origin as shown in the below.

A maltose-trehalose converting enzyme derived from Pimelobacter sp. R48 has the following physicochemical properties:

(1) Action Converting maltose into trehalose and vice versa.

Forming about one mole of trehalose from one mole of maltose or forming about one from one mole of mole of maltose trehalose;

(2) Molecular weight About 57,000–67,000 daltons on sodium dodecylsulfate polyacrylamide gel electrophoresis (SDS-PAGE);

(3) Isoelectric point (pI) About 4.1–5.1 on isoelectrophoresis using ampholyte;

(4) Inhibition of activity

Being inhibited by one mM $Cu^{++}$, $Hg^{++}$ and Tris-HCl buffer; and (5) Optimum temperature About 20° C. when incubated at pH 7.0 for 60 min;

(6) Optimum pH About 7.0–8.0 when incubated at 25° C. for 60 min;

(7) Thermal stability Being stable up to about 30° C. when incubated at pH 7.0 for 60 min; and (8) pH Stability Being stable at a pH of about 6.0–9.0 when incubated at 20° C. for 60 min.

A maltose-trehalose converting enzyme derived from *Pseudomonas putida* H262 has the following physicochemical properties:

(1) Action Converting maltose into trehalose and vice versa;

Forming about one mole of trehalose from one mole of maltose or forming about one mole of maltose from one mole of trehalose;

(2) Molecular weight About 110,000–120,000 daltons on SDS-PAGE;

(3) Isoelectric point (pI) About 4.1–5.1 on electrophoresis using ampholyte;

(4) Inhibition of activity Being inhibited by one mM $Cu^{++}$, $Hg^{++}$ and 50 mM Tris-HCl buffer;

(5) Optimum temperature

About 37° C. when incubated at pH 7.0 for 60 min;

(6) Optimum pH Being stable at a pH of about 7.3–8.3 when incubated at pH 7.0 for 60 min; and (7) Thermal stability Being stable up to 40° C. when incubated at pH 7.0 for 60 min; and (8) pH Stability Being stable at a pH of about 6.0–9.5 when incubated at 35° C. for 60 min.

The maltose-trehalose converting enzyme derived from *Thermus aquaticus* (ATCC 33923) has the following physicochemical properties:

(1) Action Converting maltose into trehalose and vice versa;

Forming about one mole of trehalose from one mole of maltose or forming about one mole of maltose from one mole of trehalose;

(2) Molecular weight About 100,000–110,000 daltons on SDS-PAGE;

(3) Isoelectric point (pI) About 3.8–4.8 on electrophoresis using ampholyte;

(4) Inhibition of activity Being inhibited by one mM $Cu^{++}$, $Hg^{++}$ and 50 mM Tris-HCl buffer;

(5) Optimum temperature About 65° C. when incubated at pH 7.0 for 60 min;

(6) Optimum pH Being stable at a pH of about 6.0–6.7 when incubated at 60° C. for 60 min;

(7) Thermal stability Being stable up to a temperature of 80° C. when incubated at pH 7.0 for 60 min; and (8) pH Stability Being stable at a pH of about 5.5–9.5 when incubated at 60° C. for 60 min.

The activity of the present maltose-trehalose converting enzyme is assayed as follows: One ml of an enzyme solution is added to one ml of 20 w/v % maltose as a substrate in 10 mM phosphate buffer (pH 7.0), and the mixture solution is incubated at 25° C., 35° C. or 60° C. for 60 min, followed by the heating the solution at 100° C. for 10 min to suspend the enzymatic reaction. To the resultant reaction mixture is precisely diluted by 11-fold with 50 mM phosphate buffer (pH 7.5), and 0.4 ml of the diluted solution is admixed with 0.1 ml of a trehalase solution having one unit/ml of trehalase. The resultant solution is incubated at 45° C. for 120 min, followed by determining the amount of glucose by the glucose-oxidase method. As a control, by using trehalase and an enzyme solution, which were preheated at 100° C. for 10 min to inactivate the enzyme, the activity of the enzyme solution is assayed similarly as above. With the above assay, the content of trehalose, formed by the present maltose-trehalose converting enzyme, is determined based on the amount of glucose formed, and one unit activity of the enzyme is defined as the amount of enzyme which forms one μmole of trehalose per minute. As regards to the reaction temperature, it is set to 25° C. for the enzyme of a microorganism of the genus Pimelobacter; 35° C. for that of the genus Pseudomonas; and 60° C. for that of the genus Thermus.

Since the present maltose-trehalose converting enzyme converts maltose into trehalose and vice versa, maltose or trehalose as a substrate can be used to meet to its final use. Maltose is used as a substrate for preparing trehalose.

Any maltose can be used in the invention as long as it is converted into trehalose when received with the action of the present maltose-trehalose converting enzyme, and, in general, high maltose content products with the highest possible purity, preferably, those with a purity of 70% or higher, d.s.b., can be suitably used. Commercially available maltose products and those prepared by conventional starch saccharification techniques are also used.

Examples of maltose preparation from starch are those disclosed in Japanese Patent Publication Nos.11,437/81 and 17,078/81 wherein β-amylase is allowed to act on gelatinized- and liquefied-starch to form maltose which is then separated from high molecular weight dextrin and recovered in a high maltose content product. Other examples are those disclosed in Japanese Patent Publication Nos.13,089/72 and 3,938/79 wherein β-amylase is allowed to act on gelatinized- and liquefied-starch together with a starch debranching enzyme such as isoamylase and pullulanase to form maltose which is then recovered in a high maltose content product.

To the concomitant saccharides such as maltotriose present in the resultant high maltose content products, prepared by the aforesaid preparations, are added the enzymes as disclosed in Japanese Patent Publication Nos.28, 153/81, 3,356/82 and 28,154/81 to increase the maltose content. The maltose content in the high maltose content products can be satisfactorily more increased by removing the concomitant saccharides on column chromatography using a strong-acid cation-exchange resin as disclosed in Japanese Patent Laid-Open No.23,799/83

The concentration of the substrates used in the invention is not specifically restricted. The enzymatic reaction of the present enzyme proceeds even in a solution of 0.1% or 50% of a material maltose, resulting in the formation of trehalose. Suspensions containing insoluble substrates can be used in the invention. The temperature used in the present enzymatic reaction can be set to a temperature at which the enzyme is not inactivated, i.e. a temperature up to about 80° C., preferably, a temperature in the range of about 0°–70° C. The reaction pH used in the present enzymatic reaction is set to a pH in the range of about 5.5–9.0, preferably, a pH in the range of about 6.0–8.5. The reaction time used in the present enzymatic reaction is adequately chosen dependently on the reaction conditions, and, usually, it is in the range of about 0.1–100 hours when the enzyme is used in an amount of about 0.1–100 units/g substrate, d.s.b.

The present enzymatic reaction enables the conversion of trehalose from a material maltose in a relatively-high conversion rate, i.e. the maximum is about 70–85%.

The reaction mixture thus obtained are in usual manner subjected to filtration and centrifugation to remove insoluble substances, and decolored with an activated charcoal, desalted with ion-exchangers in H- and OH-form, and concentrated into syrupy products. If necessary, the syrupy products can be arbitrarily dried into powdery products or prepared into crystalline products.

Furthermore, the powdery products are readily processed into high-purity trehalose products by purifying them with one or more methods, for example, fractionations by ion-exchange column chromatography and column chromatography using an activated charcoal or a silica gel; and alkaline treatments to decompose and remove the remaining reducing saccharides. Maltose separable by such a column chromatography can be suitably used as a substrate for the conversion of maltose into trehalose by the present maltose-trehalose converting enzyme.

If necessary, the present saccharide composition containing trehalose can be hydrolyzed by glucoamylase and α-glucosidase, or subjected to a saccharide-transfer reaction by using cyclomaltodextrin glucanotransferase and/or glucosyltransferase to control its sweetness, reducing power and viscosity. Furthermore, reducing saccharides in the resultant trehalose products can be arbitrarily removed by decomposing them with alkaline treatments and fermenting them with yeasts, or hydrogenated into sugar alcohols. Thus, their reducing power is eliminated. From the resultants, glucose can be removed by the above purification methods such as ion-exchange column chromatography to obtain high trehalose content fractions. The fractions thus obtained can be readily purified and concentrated into syrupy products, and, if necessary, the syrupy products can be further concentrated into supersaturated solutions and crystallized into hydrous or anhydrous crystalline trehalose.

The ion-exchange column chromatography usable in the invention includes, for example, those which employ a strong-acid cation-exchange resin as disclosed in Japanese Patent Laid-Open Nos.23,799/83 and 72,598/83. By using the column chromatography, the concomitant saccharides contained in a crude trehalose product can be readily removed to obtain high trehalose content fractions. In this case, any one of fixed-bed, moving bed and semi-moving methods can be arbitrarily employed.

In order to prepare hydrous crystalline trehalose, a 65–90% solution of trehalose with a purity of 60% or higher is placed in a crystallizer, and gradually cooled while stirring in the presence or absence of an about 0.1–20% seed crystal at a temperature of 95° C. or lower, preferably, at a temperature in the range of 10°–90° C., to obtain a massecuite containing hydrous crystalline trehalose. Continuous crystallization methods, which attain the crystallization of the objective saccharides under their concentration in vacuo, can be arbitrarily employed. Conventional methods such as separation, block pulverization, fluidized-bed granulation and spray drying can be employed in the invention to prepare from the massecuite hydrous crystalline trehalose or crystalline saccharides containing it.

In the case of separation, massecuites are usually subjected to a basket-type centrifuge to separate hydrous crystalline trehalose from a mother liquor, and, if necessary, the resultant hydrous crystalline trehalose is washed by spraying it with a small amount of cold water to facilitate the preparation of hydrous crystalline trehalose with an increased purity.

In the case of spray drying, crystalline saccharides with no or substantially free of hygroscopicity are readily prepared by spraying massecuites having a concentration of about 60–85%, d.s.b., and a crystallinity of about 20–60%, d.s.b., from a nozzle by a high-pressure pump; drying the resultants with an about 60°–100° C. hot air which does not melt the resultant crystalline powders; and aging the resultant powders for about 1–20 hours while blowing with an about 30°–60° C. hot air.

In the case of block pulverization, crystalline saccharides with no or substantially free of hygroscopicity are readily prepared by allowing massecuites having a moisture content of about 10–25% and a crystallinity of about 10–60%, d.s.b., to stand for several hours to 3 days or so in order to crystallize and solidify the whole contents into blocks, pulverizing or cutting the resultant blocks, and drying the resultants.

Although anhydrous crystalline trehalose can be prepared by drying hydrous crystalline trehalose to convert it into anhydrous form, it is generally prepared by providing a high trehalose content solution with a moisture content less than 10%, placing the solution in a crystallizer, keeping the solution in the presence of a seed crystal at a temperature in the range of 50°–160° C., preferably, at a temperature in the range of 80°–140° C. under stirring conditions to obtain a massecuite containing anhydrous crystalline trehalose, and crystallizing and pulverizing the anhydrous crystalline trehalose by conventional methods such as block pulverization, fluidized-bed granulation and spray drying under the conditions of dry and relatively-high temperature.

The present trehalose thus obtained is stable and substantially free of reducing power, and can be mixed and processed with other materials, specifically, amino acids and amino acid-containing substances such as oligopeptides and proteins without a fear of causing unsatisfactory browning and smell as well as deterioration of the materials. Trehalose per se has a satisfactorily-high quality and sweetness. Since trehalose is readily hydrolyzed by trehalase into glucoses, it is readily assimilated, absorbed and utilized by living bodies as an energy source when orally administered. Furthermore, trehalose is not substantially fermented by dental carries-inducing microorganisms, and this renders it useful as a sweetener which does not substantially induce dental caries.

The present trehalose is a stable sweetener, and, specifically, crystalline trehalose is arbitrarily used as a sugar coating agent for tablets when used in combination with a binder such as pullulan, hydroxyethyl starch or polyvinylpyrrolidone. In addition, the trehalose has properties such as osmotic pressure-controlling ability, filler-imparting ability, gloss-imparting ability, moisture-retaining ability, viscosity-imparting ability, substantial no fermentability, ability to prevent retrogradation of gelatinized starch, and ability to prevent crystallization of other saccharides.

Thus, the present trehalose and saccharide composition containing the same can be arbitrarily used as a sweetener, taste-improving agent, quality-improving agent, stabilizer and filler in a variety of compositions such as food products, cigarettes, tobaccos, feeds, cosmetics and pharmaceuticals.

The present trehalose and saccharide composition can be used intact as a seasoning for sweetening. If necessary, they can be used in combination with adequate amounts of one or more other sweeteners, for example, powdered syrup, glucose, maltose, sucrose, isomerized sugar, honey, maple sugar, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

Powdery or crystalline products containing the present trehalose or the saccharide composition can be used intact, and, if necessary, they can be mixed with an excipient, filler, diluent and binder, and formed into granules, spheres, shot-rods, plates, cubes and tablets, prior to their use.

The present saccharide composition containing trehalose with a low reducing-power and trehalose separated therefrom well harmonize with other materials having sour-, acid-, salty-, bitter-, astringent- and delicious-tastes, and have a relatively-high acid tolerance and heat resistance. Thus, they can be favorably used in food products in general as a sweetener, taste-improving agent and quality-improving agent.

The present trehalose and saccharide composition containing the same can be used in seasonings such as a soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu638 (a sauce for Japanese vermicelli), sauce, catsup, "takuan-zuke-no-moto" (a premix for pickled radish), "hakusai-zuke-no-moto" (a premix for fresh white rape pickles), "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar and coffee sugar.

The present trehalose and saccharide composition containing the same can be also used freely for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products such as milk beverage, yogurt and cheese; canned and bottled products such as those of meat, fish meat, fruit and vegetable; alcoholic beverages such as synthetic sake, wine and liquors; soft drinks such as coffee, tea, cocoa, juice, carbonated beverage, sour milk beverage and beverage containing a lactic acid bacterium; instant food products such as instant pudding mix, instant hot cake mix and "sokuseki-shiruco" (an instant mix of adzuki-bean soup with rice cake) and instant soup mix; and beverages such as baby foods, foods for therapy, and beverages supplemented with nutrition; as well as for improving the tastes and qualities of the aforementioned food-products.

The present trehalose and saccharide composition containing the same can be also used in feeds and pet foods for animals such as domestic animals, poultry, honey bees, silk worms and fishes in order to improve their taste preferences. The present trehalose and saccharide composition can be arbitrarily used as a sweetener, taste-improving agent, quality-improving agent and stabilizer in other products in paste and liquid form such as a tobacco, cigarette, dentifrice, lipstick, rouge, lip cream, internal medicine, tablet, troche, cod liver oil in the form of a drop, cachou, oral refrigerant, gargle, cosmetic and pharmaceutical.

The present trehalose and saccharide composition containing the same can be used as a quality-improving agent and stabilizer for biologically active substances susceptible to loss of their effective ingredients and activities, as well as in health foods and pharmaceutical compositions containing biologically active substances. Examples of such a biologically active substance are lymphokines such as α-, β- and γ-interferons, tumor necrosis factor-α (TNF-α), tumor necrosis factor-β (TNF-β), macrophage migration inhibitory factor, colony-stimulating factor, transfer factor and interleukin 2 (IL-2); hormones such as insulin, growth hormone, prolactin, erythropoietin, follicle-stimulating hormone, and placental hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, β-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. By using the present trehalose and saccharide composition containing the same, the aforementioned biologically active substances are readily prepared into health foods and pharmaceutical compositions with a satisfactorily-high stability and quality without a fear of losing or inactivating their activities and effective ingredients.

As described above, the methods to incorporate the present trehalose and saccharide composition containing the same into the aforementioned substances and compositions include conventional methods, for example, mixing, kneading, dissolving, melting, soaking, permeating, sprinkling, applying, coating, spraying, injecting, crystallizing and solidifying. The trehalose and saccharide composition are usually incorporated into the aforementioned substances and compositions in an amount of 0.1% or higher, preferably, one % or higher, d.s.b.

The following experiments explain the present invention more in detail:

EXPERIMENT 1

Production of Enzyme

One hundred ml aliquots of a liquid nutrient culture medium, consisting of 2.0 w/v % glucose, 0.5 w/v % polypeptone, 0.1 w/v % yeast extract, 0.06 w/v % disodium hydrogenphosphate, 0.1 w/v % potassium hydrogenphosphate, 0.05 w/v % magnesium sulfate heptahydrate, 0.5 w/v % calcium carbonate and water, were placed in 500-ml Erlenmeyer flasks, autoclaved at 115° C. for 30 min to effect sterilization, cooled, and inoculated with a seed culture of Pimelobacter sp. R48 (FERM BP-4315), followed by the cultivation at 27° C. for 24 hours under stirring conditions of 200 rpm. The resultant cultures were pooled and used as a seed culture.

About 20 L aliquot of a fresh preparation of the same liquid nutrient culture medium as used in the above culture was placed in a 30-L fermenter, sterilized, cooled to 27° C., and inoculated with one v/v % of the seed culture, followed by the culture at 27° C. and a pH of 6.0–8.0 for about 40 hours under stirring and aerobic conditions.

The activity of a maltose-trehalose converting enzyme accumulated in the resultant culture was 0.55 units/ml. A portion of the culture was separated by centrifugation into cells and a supernatant, and the cells were suspended in 50 mM phosphate buffer (pH 7.0) to give the same volume of that of the portion, followed by assaying the enzyme activity in the cell suspension and the supernatant to give 0.5 units/ml and 0.05 units/ml respectively. The enzyme activity was the value assayed at 25° C.

EXPERIMENT 2

Purification of Enzyme

The culture obtained in Experiment 1 was centrifuged to obtain an about 0.5 kg wet cells which were then suspended in 10 mM phosphate buffer (pH 7.0). The cell suspension was subjected to "VIBROGEN-ZELLMÜHLE", a cell disrupting apparatus commercialized by Edmund Bühler, Tubingen, Germany, and the resultant mixture was centrifuged at 15,000×g for 30 min to obtain an about 4.5 L supernatant. Ammonium sulfate was added to the supernatant and dissolved therein to give a saturation degree of 0.3, and the solution was allowed to stand at 4° C. for 4 hours, and centrifuged to obtain a supernatant.

Ammonium sulfate was further added to the resultant supernatant and dissolved therein to give a saturation degree of 0.8, and the solution was allowed to stand at 4° C. overnight, and centrifuged to obtain a sediment.

The sediment was dissolved in 10 mM phosphate buffer (pH 7.0), dialyzed against a fresh preparation of the same buffer for 24 hours, and centrifuged to remove insoluble substances. Four hundred ml of the resultant dialyzed solution was divided into 2 portions which were then separately subjected to column chromatography using a column packed with 300 ml of "DEAE-TOYOPEARL®GEL", an ion-exchanger commercialized by Tosoh Corporation, Tokyo, Japan.

The present maltose-trehalose converting enzyme adsorbed on the ion-exchanger was eluted from the column with a fresh preparation of the same buffer supplemented with salt. Fractions with the enzyme activity eluted from the column were recovered, pooled and dialyzed against a fresh preparation of the same buffer supplemented with one M ammonium sulfate. The dialyzed solution was centrifuged to remove insoluble substances, and subjected to hydrophobic column chromatography using a column packed with 300 ml of "BUTYL-TOYOPEARL®650 GEL", a hydrophobic gel commercialized by Tosoh Corporation, Tokyo, Japan. The maltose-trehalose converting enzyme adsorb on the gel was eluted from the column with a liner gradient buffer ranging from 1 M to 0 M ammonium sulfate, followed by recovering fractions with the enzyme activity.

The fractions were pooled and subjected to ion-exchange column chromatography using a column packed with 10 ml of "MONO Q HR5/5", a gel commercialized by Pharmacia LKB Biotechnology AB, Uppsala, Sweden, followed by recovering fractions with the enzyme activity. The total activity, specific activity and yield in each purification step are tabulated in Table 1.

TABLE 1

| Purification step | Total enzyme* activity (units) | Specific activity (units/ mg protein) | Yield (%) |
| --- | --- | --- | --- |
| Supernatant after cell disruption | 7,310 | 0.25 | 100 |
| Dialyzed solution after salting out | 2,730 | 0.31 | 37.3 |
| Eluate from ion-exchange column | 2,290 | 1.35 | 31.3 |
| Eluate from hydrophobic column | 1,160 | 10.8 | 15.9 |
| Eluate from ion-exchange column | 819 | 33.6 | 11.2 |

Note:
The symbol "*" means the present maltose-trehalose converting enzyme.

The purified enzyme preparation obtained by the above purification procedure was electrophoresed by using a 7.5% sodium dodecylsulfate polyacrylamide gel to give a single protein band, and this meant that it was a considerably-high purity preparation.

EXPERIMENT 3

Property of Enzyme

A portion of a purified maltose-trehalose converting enzyme preparation, obtained by the method in Experiment 2, was electrophoresed by using a 10% sodium dodecylsulfate polyacrylamide gel. The molecular weight was determined to be about 57,000–67,000 daltons by comparing it with those of marker proteins, commercialized by Japan Bio-Rad Laboratories, Tokyo, Japan, which had been simultaneously electrophoresed.

Another portion of the purified maltose-trehalose converting enzyme preparation was isoelectrophoresed by using a polyacrylamide gel containing 2 v/v % "AMPHOLINE", an ampholyte commercialized by Pharmacia LKB Biotechnology AB, Uppsala, Sweden. The resultant gel was sliced into pieces, followed by measuring their pHs to reveal the pI of the enzyme being about 4.1–5.1.

Figure 2:
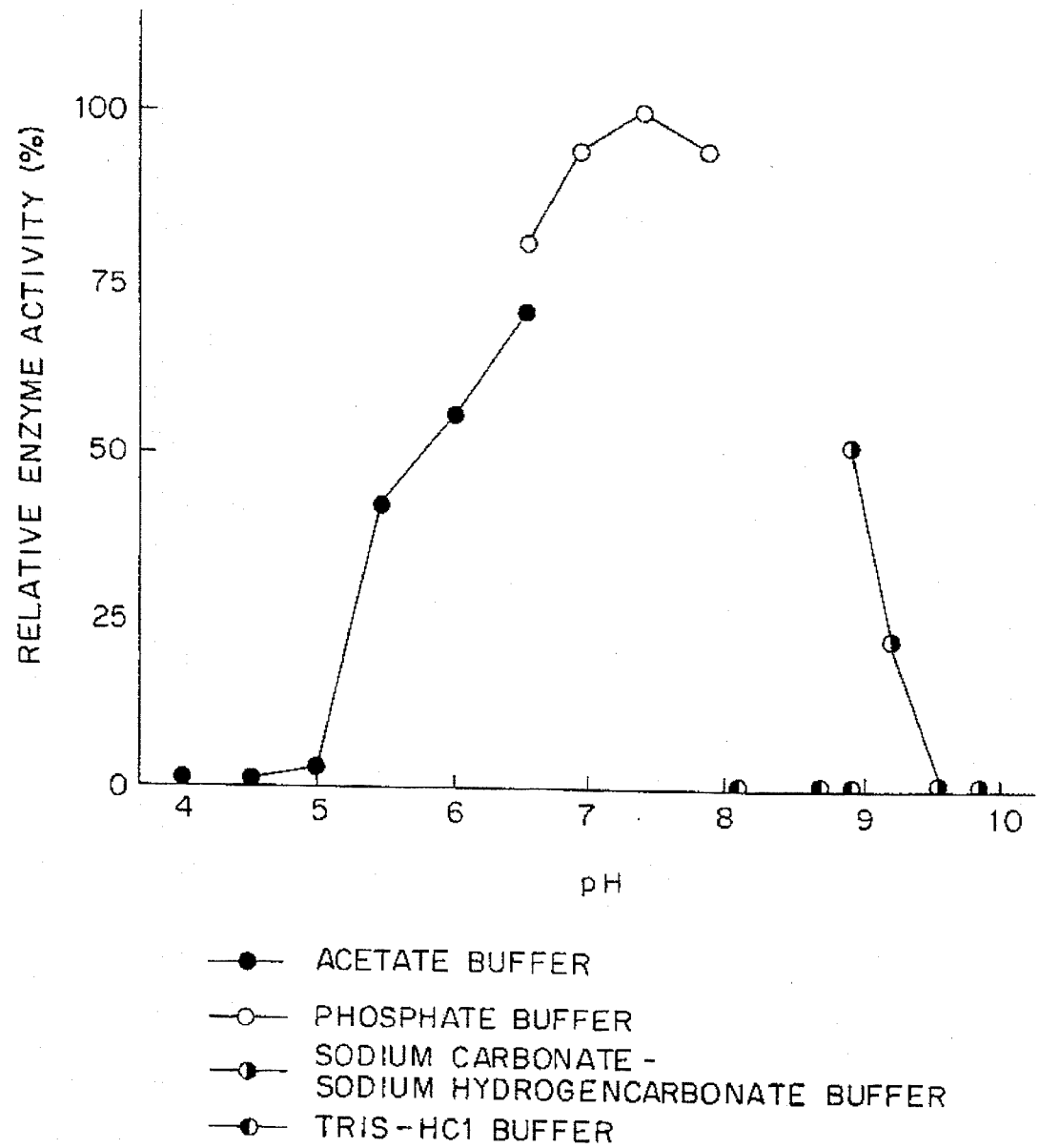
FIG. 2 shows the influence of pH on the enzyme activity of the present maltose-trehalose converting enzyme derived from Pimelobacter sp. R48.
Figure 3:
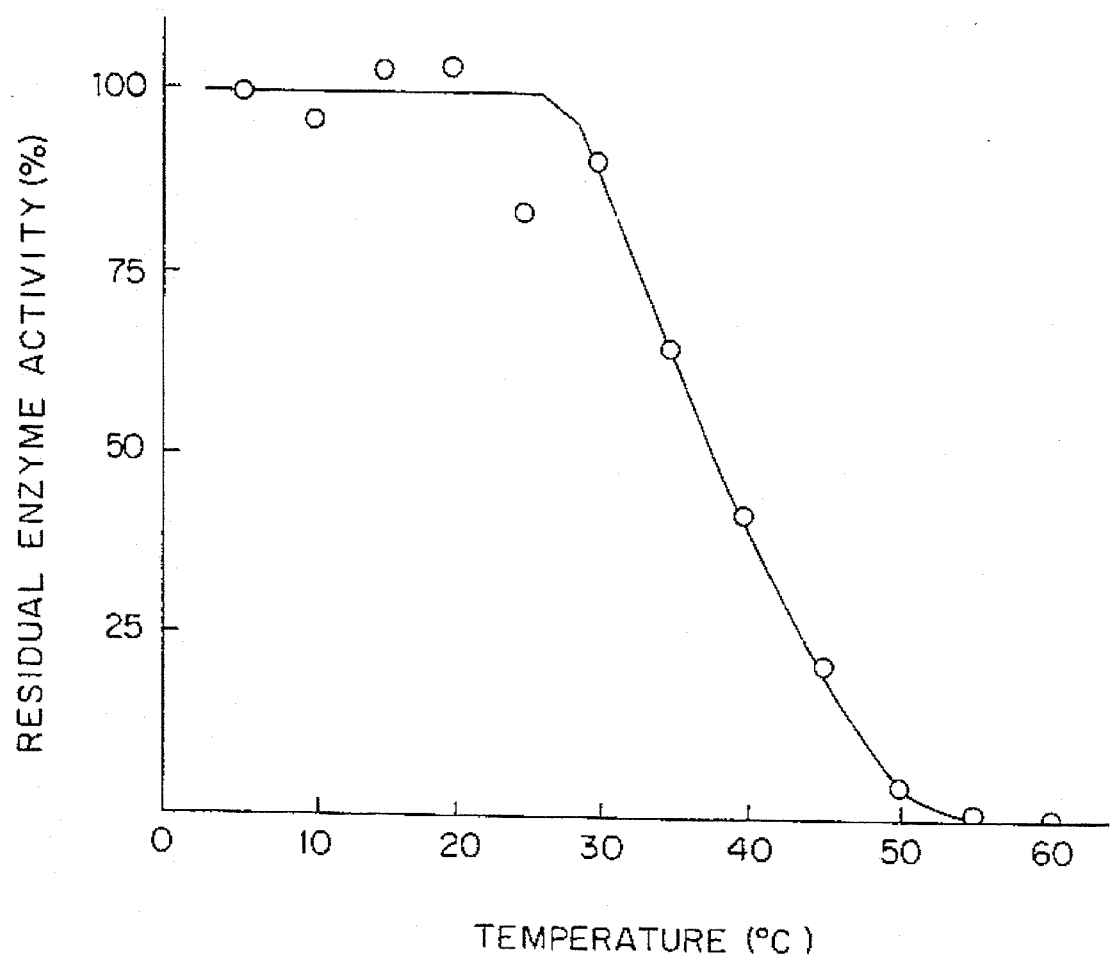
FIG. 3 shows the influence of temperature on the stability of the present maltose-trehalose converting enzyme derived from Pimelobacter sp. R48.
Figure 4:
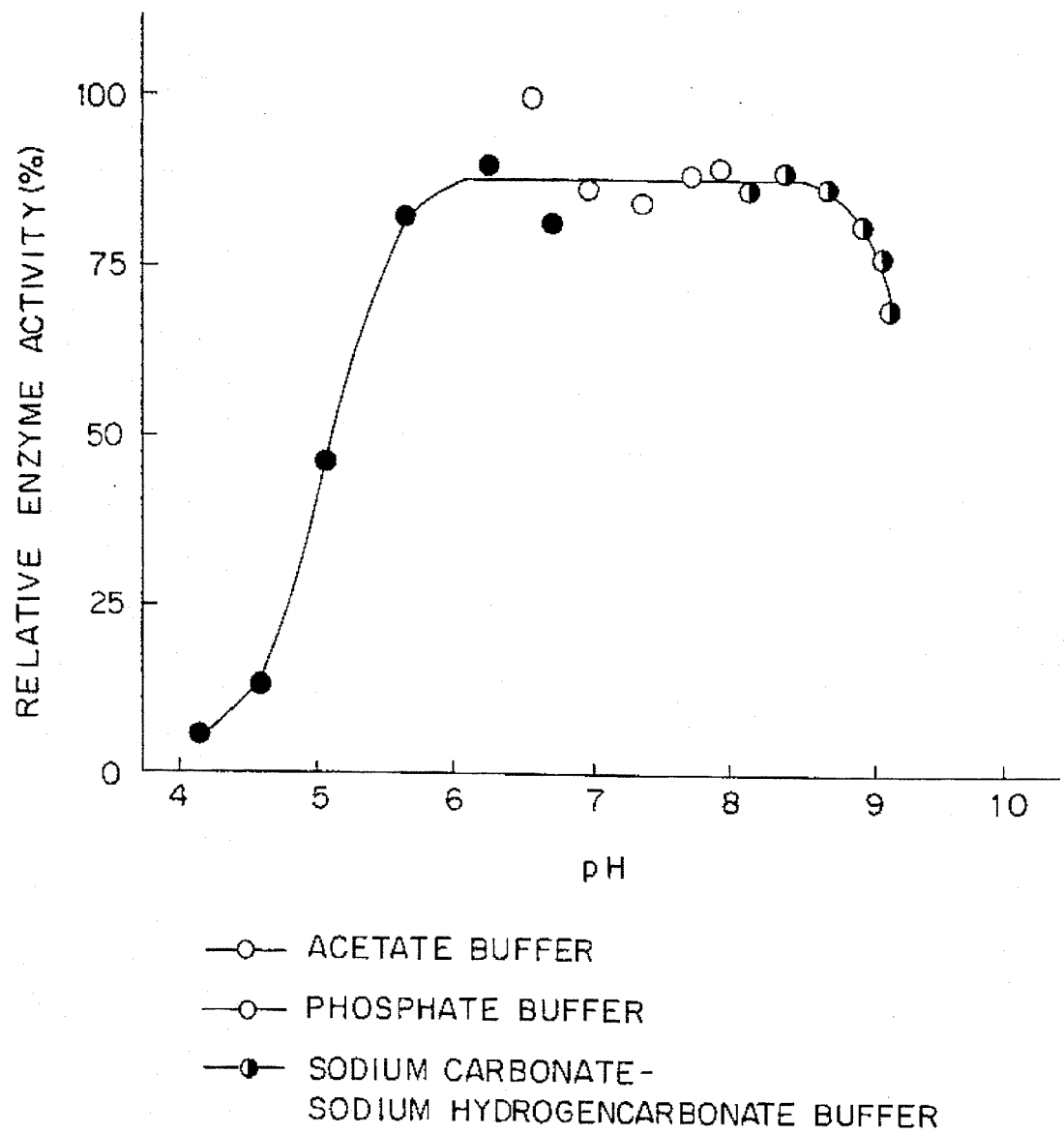
FIG. 4 shows the influence of pH on the stability of the present maltose-trehalose converting enzyme derived from Pimelobacter sp. R48.

Effects of temperature and pH on the activity of the present enzyme were studied in accordance with the method as used for assaying the enzyme activity. The results were respectively shown in FIG. 1 (effect of temperature) and FIG. 2 (effect of pH). The optimum temperature of the enzyme was about 20° C. when incubated at pH 7.0 for 60 min, and the optimum pH was about 7.0–8.0 when incubated at 25° C. for 60 min. The thermal stability of the enzyme was determined by incubating it in 50 mM phosphate buffers (pH 7.0) in test tubes at different temperatures for 60 min, cooling the test tubes with cold water, and assaying the residual enzyme activity in each buffer. The pH stability of the enzyme was determined by incubating it in 50 mM phosphate buffers having different pHs at 20° C. for 60 min, adjusting the buffers to pH 7.0, and assaying the residual enzyme activity in each buffer. The results of the thermal- and pH-stabilities of the enzyme were respectively shown in FIGS. 3 and 4. The enzyme was stable up to a temperature of about 30° C. and stable at a pH of about 6.0–9.0. One mM $Cu^{++}$ or $Hg^{++}$ and 50 mM Tris-HCl buffer were inhibitory to the enzyme.

EXPERIMENT 4

Action on Saccharides

A variety of saccharides were tested for determining whether they could be used as a substrate for the present enzyme. Glucose, maltose, maltotriose, maltotetraose, maltopentaose, maltohexaose, maltoheptaose, soluble starch, amylose having an average polymerization degree of 18, trehalose, neotrehalose, gentiobiose, kojibiose, isomaltose, cellobiose, maltitol, sucrose, maltulose, turanose, paratinose, trehalulose or lactose was prepared into a solution. A solution containing glucose and the equal amount of α-glucose 1-phosphate or β-glucose 1-phosphate was prepared.

The solutions were respectively mixed with 2 units/g substrate, d.s.b., of a maltose-trehalose converting enzyme obtained by the method in Experiment 2, adjusted their substrate concentrations to 5 w/v %, and subjected to an enzymatic reaction at 20° C. and pH 7.0 for 24 hours. The solutions before and after their enzymatic reactions were subjected to thin layer chromatography (TLC) using "KIESELGEL 60 (20×20 cm)", an aluminum plate for TLC commercialized by Merck & Co., Inc., Rahway, USA, for determining whether the present enzyme acts on the saccharides. The resultant products were developed once on the plates by using a developing solvent system of 1-butanol, pyridine and water (=6:4:1 by volume). The products on the plates were colored by spraying thereto a 20 v/v % sulfuric acid in methanol, and heating the plates at 110° C. for 10 min. The results were as shown in Table 2.

TABLE 2

| Substrate | Action of enzyme | Substrate | Action of enzyme |
| --- | --- | --- | --- |
| Glucose | – | Cellobiose | – |
| Maltose | ++ | Maltitol | – |
| Maltotriose | – | Sucrose | – |
| Maltotetraose | – | Maltulose | – |
| Maltopentaose | – | Turanose | – |
| Maltohexaose | – | Paratinose | – |
| Maltoheptaose | – | Trehalulose | – |
| Soluble starch | – | Lactose | – |
| Amylose (average polymerization degree of 18) | – | α-Glucose 1-phosphate plus glucose | – |
| Trehalose | + | β-Glucose 1- | – |

TABLE 2-continued

| Substrate | Action of enzyme | Substrate | Action of enzyme |
| --- | --- | --- | --- |
| Neotrehalose | – | phosphate plus glucose | |
| Neotrehalose | – | | |
| Gentiobiose | – | | |
| Kojibiose | – | | |
| Isomaltose | – | | |

Note:
In the table, the symbol "–" means that no change was observed before and after the enzymatic reaction; the symbol "+", the size of the substrate spot was slightly reduced because of the formation of other products; and the symbol "++", the size of the substrate spot was considerably reduced because of the formation of other products.

As is evident from the results in Table 2, it was revealed that the present enzyme only acts on maltose and trehalose among other saccharides, and, especially, does not act on both a system containing glucose and α-glucose 1-phosphate or β-glucose 1-phosphate. These results concluded that the present enzyme is a novel enzyme differing from conventional maltose- and trehalose-phosphorylases.

EXPERIMENT 5

Products From Maltose or Trehalose

To an aqueous maltose solution was added 2 units/g maltose as a substrate, d.s.b., of a maltose-trehalose converting enzyme obtained by the method in Experiment 2 to give a final substrate concentration of 5 w/v %, and the resultant solution was subjected to an enzymatic reaction at 20° C. and pH 7.0 for 24 hours. The saccharide composition of the resultant reaction mixture was analyzed on gas chromatography (hereinafter abbreviated as "GLC"). A portion of the reaction mixture was dried, dissolved in pyridine and trimethylsilylated to obtain a product, a sample for analysis. The apparatus and conditions used in the GLC analysis were "CG- 16A", a gas chromatograph commercialized by Shimadzu Corporation, Tokyo, Japan; a stainless-steel column, 3 mm in diameter and 2 m in length, packed with 2% "SILICONE OV-17/CHROMOSORB W" commercialized by GL Sciences Inc., Tokyo, Japan; a flow rate of 40 ml/min of nitrogen gas as a carrier gas; and a ratio of increasing temperature in an oven, 7.5° C./min ranging from 160° C. to 320° C. The saccharide composition was analyzed on a hydrogen flame ionization detector. The results were as shown in Table 3.

TABLE 3

| Saccharide in reaction mixture | GLC retention time (min) | Saccharide composition (%) |
| --- | --- | --- |
| Glucose | 3.87 and 4.70 | 4.9 |
| Maltose | 11.93 and 12.27 | 22.3 |
| X | 12.34* | 72.8 |

Note:
The value of the symbol "*" accords with that of trehalose.

As is evident from the results in Table 3, it was revealed that the product "X" formed in quantity, and the retention time accorded with that of a commercially available trehalose. In order to identify the product "X", the following confirmation test was conducted. A fresh preparation of the same aqueous maltose solution as used in the above was diluted with 20 mM acetate buffer (pH 4.5) to give a maltose concentration of 2 w/v %, and 0.5 ml of which was mixed with 0.1 unit of a glucoamylase specimen commercialized by Seikagaku-Kogyo Co., Ltd., Tokyo, Japan, followed by subjecting the mixture to an enzymatic reaction at 40° C. for 20 hours.

Similarly, a fresh preparation of the same aqueous maltose solution as used in the above was diluted with 20 mM acetate buffer (pH 7.0) to give a maltose concentration of 2 w/v %, and 0.5 ml of which was mixed with 0.5 units of trehalase, followed by subjecting the mixture to an enzymatic reaction at 40° C. for 20 hours. The intact aqueous maltose solution and the aqueous maltose solutions treated with glucoamylase and trehalase were analyzed on GLC, followed by studying the data to reveal that maltose was completely decomposed into glucoses by glucoamylase, but the product "X" remained intact.

When treated with trehalase, maltose remained intact, but the product "X" was completely decomposed into glucoses. In view of the reaction mechanisms of glucoamylase and trehalase, it was concluded that the present enzyme forms from maltose an oligosaccharide, i.e. trehalose.

Furthermore, the purified enzyme according to the present invention was allowed to act on trehalose as a substrate under the same conditions as used in the case of maltose, and the resultant reaction mixture was analyzed on GLC. The data confirmed that the present enzyme forms maltose from trehalose. The results were as shown in Table 4.

TABLE 4

| Substrate | A | B (%) | C (%) | D (%) |
|---|---|---|---|---|
| Maltose | Glucose | 4.9 | 27.9 | 78.5 |
| | Maltose | 22.3 | 0.0 | 21.5 |
| | Trehalose | 72.8 | 72.1 | 0.0 |
| Trehalose | Glucose | 3.2 | 19.9 | 83.3 |
| | Maltose | 17.2 | 0.0 | 16.7 |
| | Trehalose | 79.6 | 80.1 | 0.0 |

Note:
In the table, the symbol "A" means saccharides in the reaction mixture; the symbol "B", the saccharide composition of the reaction mixture formed by the present enzyme; the symbol "C", the saccharide composition of the reaction mixture treated with glucoamylase; and the symbol "D", the saccharide composition treated with trehalase.

As is evident from the results in Table 4, the present enzyme converts maltose into trehalose and vice versa. It was revealed that the equilibrium position of the conversion reaction inclined to the trehalose formation, i.e. the conversion rate of maltose into trehalose was about 70% or higher which was higher than that of trehalose into maltose.

EXPERIMENT 6

Influence of Maltose Concentration on Trehalose Formation

A solution containing 2.5, 5, 10, 20 or 40 w/v % maltose was mixed with 2 units/g maltose, d.s.b., of a purified maltose-trehalose converting enzyme obtained by the method in Experiment 2, and enzymatically reacted at 20° C. and pH 7.0. During the enzymatic reaction, the reaction mixture was sampled and heated at 100° C. for 10 min to inactivate the enzyme.

The total sugar content of the reaction mixture was determined by the anthrone-sulfuric acid method. The reducing sugar content was quantified in terms of glucose by the Somogyi-Nelson method, and the reducing power was determined as a ratio of the reducing sugar content against the total sugar content.

The sample was diluted to give a saccharide concentration of about one w/v % which was then subjected to "MOL-CUT II LGC", Japan Millipore Ltd., Tokyo, Japan, to removed protein, and analyzed for its saccharide composition on high-performance liquid chromatography (hereinafter abbreviated as "HPLC"). The apparatus and conditions used in the analysis were "CCPD SYSTEM", an HPLC apparatus commercialized by Tosoh Corporation, Tokyo, Japan; "YMC-PACK PA-03", a column, having a diameter of 4.6 mm and a length of 250 mm, commercialized by YMC Co., Ltd., Tokyo, Japan; an eluent system of acetonitrile and water (=78:22 by volume); a flow rate of 1.2 ml/min; and a differential refractometer as a detector. The results were as shown in Table 5.

TABLE 5

| Concentration of maltose (%) | Reaction time (hour) | Reducing power (%) | Saccharide composition (%) | | |
|---|---|---|---|---|---|
| | | | Glucose | Maltose | Trehalose |
| | 0 | 50.3 | 0.0 | 100.0 | 0.0 |
| 2.5 | 2 | 36.7 | 1.3 | 68.8 | 29.9 |
| | 8 | 21.2 | 2.5 | 38.7 | 58.8 |
| | 23 | 12.3 | 3.8 | 17.2 | 79.0 |
| | 48 | 14.5 | 5.9 | 17.1 | 77.0 |
| 5.0 | 2 | 34.8 | 1.9 | 65.3 | 32.8 |
| | 8 | 20.2 | 2.6 | 35.7 | 61.7 |
| | 23 | 12.0 | 3.2 | 17.3 | 79.5 |
| | 48 | 14.2 | 5.7 | 17.3 | 77.0 |
| 10.0 | 2 | 32.2 | 1.3 | 63.0 | 35.7 |
| | 8 | 19.7 | 2.2 | 34.2 | 63.6 |
| | 23 | 12.5 | 3.6 | 17.5 | 78.9 |
| | 48 | 14.0 | 6.1 | 17.4 | 76.5 |
| 20.0 | 2 | 34.2 | 2.0 | 63.7 | 34.3 |
| | 8 | 20.2 | 2.9 | 35.1 | 62.0 |
| | 23 | 12.9 | 3.4 | 17.4 | 79.2 |
| | 48 | 15.1 | 6.0 | 17.4 | 76.6 |
| 40.0 | 2 | 34.8 | 1.6 | 68.2 | 30.2 |
| | 8 | 21.2 | 2.7 | 38.6 | 58.7 |
| | 23 | 12.8 | 3.7 | 17.7 | 78.6 |
| | 48 | 14.9 | 5.7 | 17.5 | 76.8 |

As is evident from the results in Table 5, the conversion reaction of maltose into trehalose smoothly proceeded independently on the maltose concentration in a conversion rate of about 80%.

EXPERIMENT 7

Effect of Temperature on Trehalose Formation

A 20 w/v % maltose solution was mixed with 2 units/g maltose, d.s.b., of a purified maltose-trehalose converting enzyme obtained by the method in Experiment 2, and subjected to an enzymatic reaction at 5°, 10°, 15°, 20° or 25° C. During the enzymatic reaction, the reaction mixture was sampled at a prescribed time interval, and the samples were heated at 100° C. for 10 min to inactivate the enzyme. Similarly as in Experiment 6, the saccharide composition of the sample was analyzed on HPLC. The trehalose contents in the samples, which had been sampled at different temperatures and reaction times, were as shown in Table 6.

TABLE 6

| Reaction time | Trehalose content | | | | |
|---|---|---|---|---|---|
| (hour) | 5° C. | 10° C. | 15° C. | 20° C. | 25° C. |
| 2 | 26.1 | 28.9 | 32.9 | 34.6 | 34.7 |
| 8 | 49.5 | 54.3 | 61.2 | 62.0 | 61.1 |
| 23 | 78.2 | 79.5 | 80.9 | 79.2 | 76.7 |
| 48 | 81.8 | 80.9 | 80.4 | 76.6 | 72.7 |

As is evident from the results in Table 6, the trehalose formation rate tended to increase as the reaction temperature increased, and the conversion reaction from maltose into trehalose smoothly proceeded even at 5° C. in a trehalose conversion rate of about 82%.

EXPERIMENT 8

Preparation of Trehalose From Maltose

Ten parts by weight of maltose commercialized by Hayashibara Biochemical Laboratories, Inc., Okayama, Japan, was dissolved in 40 parts by weight of water, and the solution was mixed with 2 units/g maltose, d.s.b., of a purified maltose-trehalose converting enzyme obtained by the method in Experiment 2, and subjected to an enzymatic reaction at 15° C. and pH 7.0 for 48 hours, followed by heating the resultant reaction mixture at 100° C. for 10 min to inactivate the remaining enzyme. The reaction mixture, containing about 74% trehalose, d.s.b., was decolored with an activated charcoal, desalted with ion-exchangers in H- and OH-form, concentrated into an about 78 w/v % solution which was then mixed with 0.1% crystalline trehalose as a seed crystal, d.s.b., followed by allowing it to stand at ambient temperature overnight to effect crystallization. The resultant massecuite was separated into a crystal which was then sprayed and washed with a small amount of water, followed by the recovery of an about 3.0 parts by weight of a high-purity crystalline trehalose with a purity of 99.8%, d.s.b.

EXPERIMENT 9

Production of Enzyme

One hundred ml aliquots of a liquid nutrient culture medium, consisting of 2.0 w/v % glucose, 1.0 w/v % ammonium sulfate, 0.1 w/v % dipotassium hydrogenphosphate, 0.06 w/v % sodium dihydrogenphosphate, 0.05 w/v % magnesium sulfate, 0.3 w/v % calcium carbonate and water, were placed in 500-ml Erlenmeyer flasks, autoclaved at 115° C. for 30 min to effect sterilization, cooled, and inoculated with a seed culture of *Pseudomonas putida* (FERM BP-4579), followed by the culture at 27° C. for 24 hours under stirring conditions of 200 rpm. The resultant cultures were pooled and used as a seed culture.

About 20 L aliquot of a fresh preparation of the same liquid nutrient culture medium as used in the above culture was placed in a 30-L fermenter, sterilized, cooled to 27° C., and inoculated with one v/v % of the seed culture, followed by the culture under stirring and aerobic conditions at 27° C. and a pH of 6.5–8.0 for about 20 hours.

The activity of a maltose-trehalose converting enzyme, accumulated in the resultant culture, was 0.12 units/mi. A portion of the culture was centrifuged to separate cells and a supernatant, and the cells were suspended in 50 mM phosphate buffer (pH 7.0) to give the same volume of that of the portion, followed by assaying the enzyme activities in the cell suspension and the supernatant to reveal 0.11 units/ml and 0.01 units/ml respectively. The enzyme activity was assayed at 35° C.

EXPERIMENT 10

Purification the Enzyme

The culture obtained in Experiment 9 was centrifuged to obtain an about 0.45 kg of wet cells which were then suspended in 10 mM phosphate buffer (pH 7.0). About 2 L of the resultant cell suspension was treated with "MINI-RABO", a super-pressure cell disrupting apparatus commercialized by Dainippon Pharmaceutical Co., Ltd., Tokyo, Japan, to disrupt cell, and the resultant mixture was centrifuged at 15,000×g for 30 min to obtain an about 1.7 L supernatant. Ammonium sulfate was added to the supernatant and dissolved therein to give a saturation degree of 0.7, allowed to stand at 4° C. for 4 hours, and centrifuged to obtain the resultant sediment.

The sediment was dissolved in 10 mM phosphate buffer (pH 7.0), and the solution was dialyzed against a fresh preparation of the same buffer for 24 hours, and centrifuged to remove insoluble substances. Four hundred ml of the dialyzed solution was divided into two portions, which were respectively subjected to ion-exchange column chromatography using a column packed with 300 ml of "DEAE-TOYOPEARL®GEL", a gel commercialized by Tosoh Corporation, Tokyo, Japan.

The present maltose-trehalose converting enzyme adsorbed on the gel, and eluted therefrom with a fresh preparation of the same buffer supplemented with salt. The fractions with the enzyme activity were recovered, and subjected to ion-exchange column chromatography using a column packed with 80 ml of "DEAE-TOYOPEARL®GEL". The maltose-trehalose converting enzyme adsorbed on the gel was eluted therefrom with a liner gradient of salt ranging from 0.1 M to 0.3 M, followed by recovering fractions with the enzyme activity.

The fractions were pooled and subjected to gel filtration column chromatography using a column packed with 400 ml of 637 TOYO-PEARL HW-55S", a gel commercialized by Tosoh Corporation, Tokyo, Japan, followed by recovering the eluted fractions with the enzyme activity. The total activity, specific activity and yield in each purification step are tabulated in Table 7.

TABLE 7

| Purification step | Total enzyme* activity (units) | Specific activity (units/ mg protein) | Yield (%) |
| --- | --- | --- | --- |
| Supernatant after cell disruption | 1,750 | 0.04 | 100 |
| Dialyzed solution after salting out | 1,200 | 0.07 | 68.5 |
| First eluate from ion-exchange column | 1,090 | 0.53 | 62.3 |
| Second eluate from ion-exchange column | 360 | 4.5 | 20.6 |
| Eluate from gel filtration column | 156 | 6.5 | 8.9 |

Note:
The symbol "*" means the present maltose-trehalose converting enzyme.

The purified enzyme preparation was subjected to gel electrophoresis using 7.5 w/v % sodium dodecylsulfate polyacrylamide gel, and found as a single protein band which meant that it was a relatively-high purity preparation.

EXPERIMENT 11

Property of Enzyme

A portion of a purified maltose-trehalose converting enzyme preparation, obtained by the method in Experiment 10, was electrophoresed by using a 7.5 w/v % sodium dodecylsulfate polyacrylamide gel, and determined its molecular weight to be about 110,000–120,000 daltons by comparing it with those of marker proteins, commercialized by Japan Bio-Rad Laboratories, Tokyo, Japan, which had been simultaneously electrophoresed.

Another portion of the purified maltose-trehalose converting enzyme preparation was isoelectrophoresed by using a polyacrylamide gel containing 2 w/v % "AMPHOLINE", an ampholyte commercialized by Pharmacia LKB Biotechnology AB, Uppsala, Sweden. Thereafter, the resultant gel was sliced into pieces, followed by measuring their pHs to reveal the pI of the enzyme being about 4.1–5.1.

Figure 5:
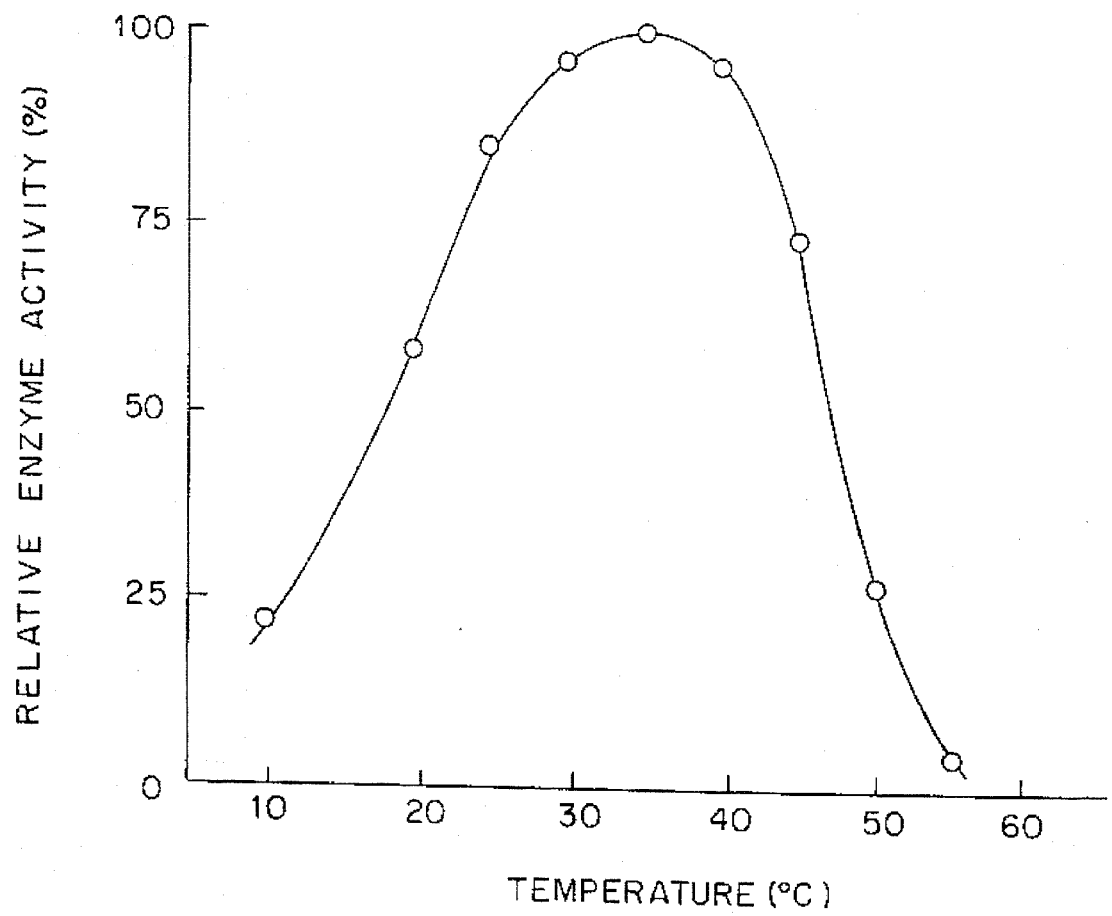
FIG. 5 shows the influence of temperature on the enzyme activity of the present maltose-trehalose converting enzyme derived from *Pseudomonas putida* H262.
Figure 6:
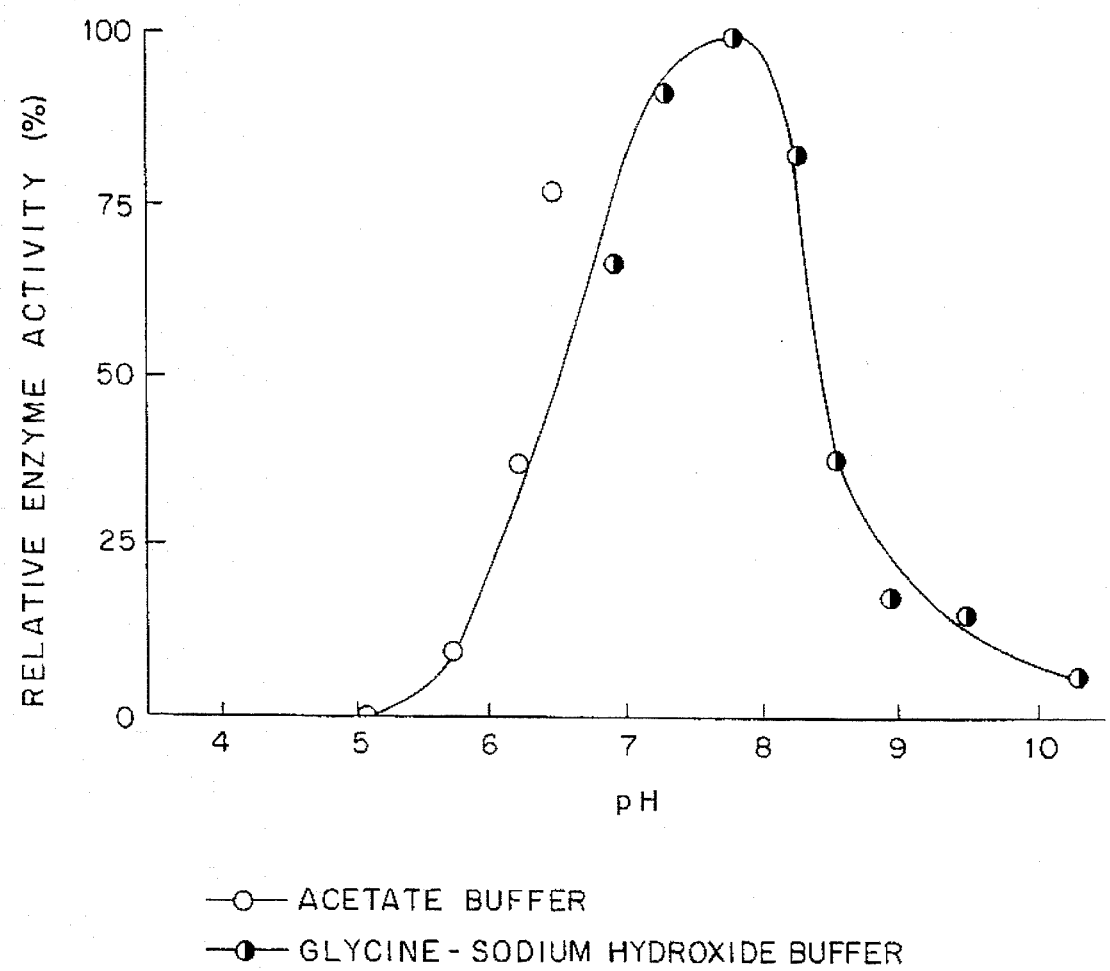
FIG. 6 shows the influence of pH on the enzyme activity of the present maltose-trehalose converting enzyme derived from *Pseudomonas putida* H262.
Figure 7:
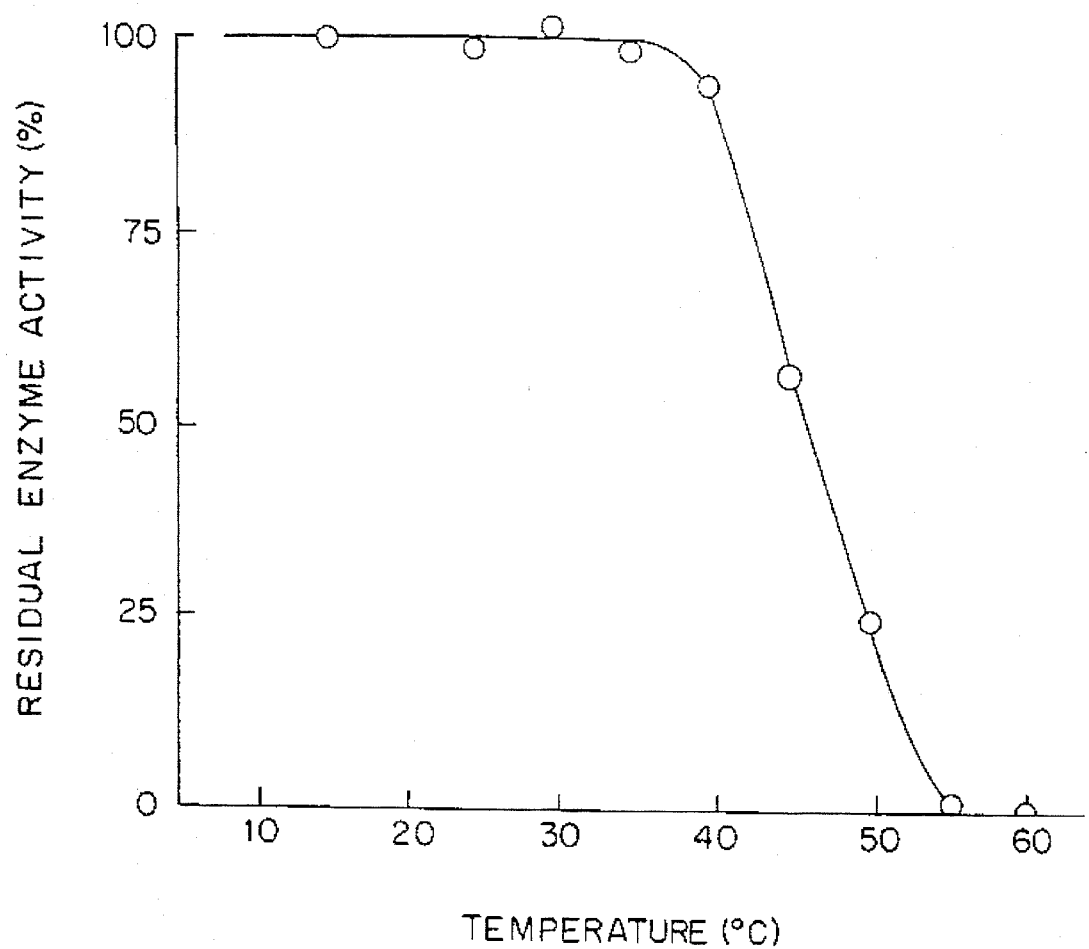
FIG. 7 shows the influence of temperature on the stability of the present maltose-trehalose converting enzyme derived from *Pseudomonas putida* H262.
Figure 8:
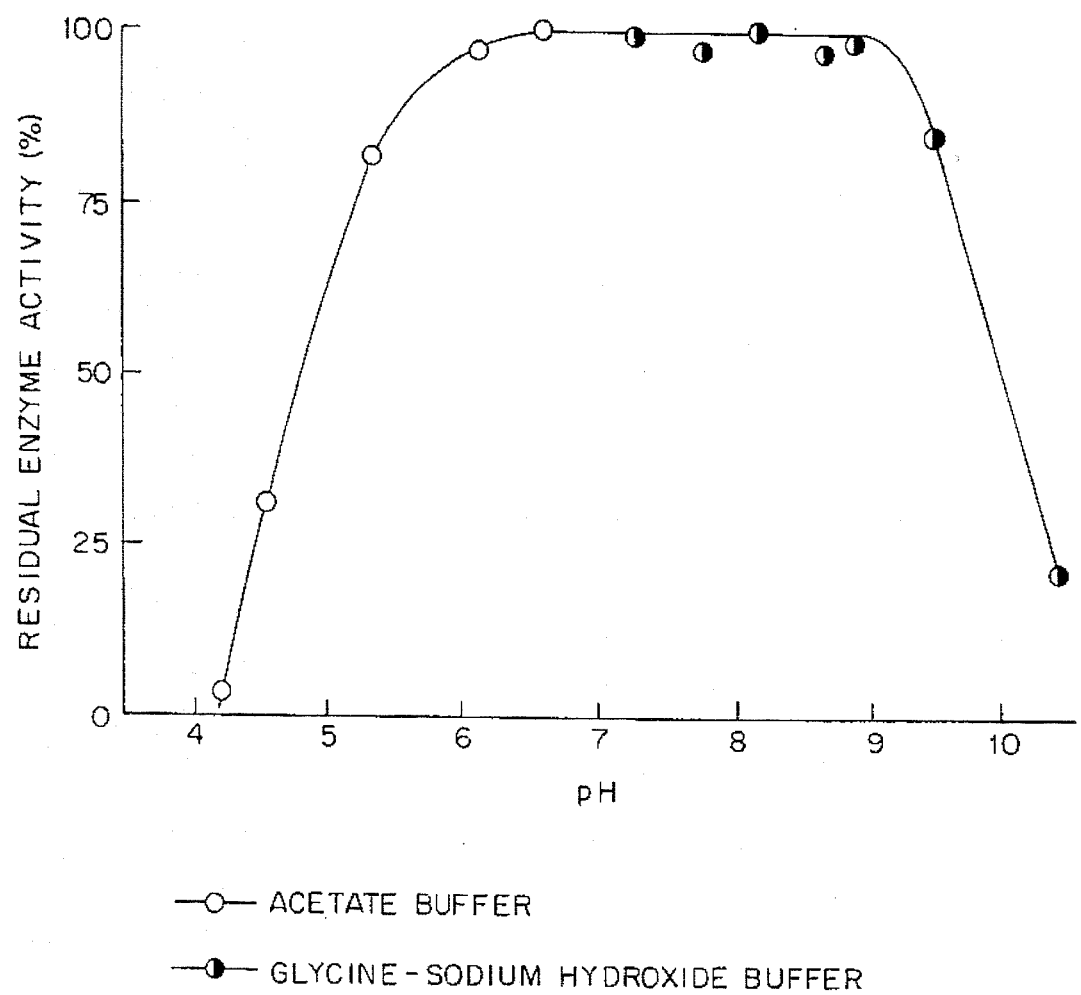
FIG. 8 shows the influence of pH on the stability of 5the present maltose-trehalose converting enzyme derived from *Pseudomonas putida* H262.

Effects of temperature and pH on the activity of the present enzyme were studied in accordance with the method as used for assaying the enzyme activity. The results were respectively shown in FIG. 5 (effect of temperature) and FIG. 6 (effect of pH). The optimum temperature of the enzyme was about 20° C. when incubated at pH 7.0 for 60 min and the optimum pH was about 7.3–8.3 when incubated at 35° C. for 60 min. The thermal stability of the enzyme was determined by incubating it in containers with 50 mM phosphate buffers (pH 7.0) at different temperatures for 60 min, cooling the resultant buffers in the containers with cold water, and assaying the residual enzyme activity in each buffer. The pH stability of the enzyme was determined by incubating it in 50 mM phosphate buffers having different pHs at 35° C. for 60 min, adjusting the resultant buffers to pH 7.0, and assaying the residual enzyme activity in each buffer. The results of the thermal- and pH-stabilities of the enzyme were respectively shown in FIGS. 7 and 8. The enzyme was stable up to a temperature of about 40° C. and stable at a pH of about 6.0–9.5. One mM $Cu^{++}$ or $Hg^{++}$ and 50 mM Tris-HCl buffer were inhibitory to the present enzyme.

EXPERIMENT 12

Action on Saccharides

A variety of saccharides were tested for determining whether they could be used as a substrate for the present enzyme from *Pseudomonas putida* H262 obtained in Experiment 10 in accordance with the method in Experiment 4 except for setting the reaction temperature to 35° C. Similarly as the enzyme from *Pseudomonas putida* H262, the enzyme from *Pimelobacter* sp. R48 specifically acted on maltose and trehalose, i.e., it converted maltose into trehalose and vice versa. It was revealed that the equilibrium position of the conversion reaction inclined to the formation of trehalose, i.e. the conversion rate of maltose into trehalose was as high as about 70%.

EXPERIMENT 13

Influence of Maltose Concentration on the Formation of Trehalose

To a solution containing 5, 10, 20 or 30% maltose was added 2 units/g maltose, d.s.b., of a purified maltose-trehalose converting enzyme obtained by the method in Experiment 10, and the solution was subjected to an enzymatic reaction at 35° C. and pH 7.0 while sampling the reaction mixture at a prescribed time interval. The samples were heated at 100° C. for 10 min to inactivate the remaining enzyme.

The samples were determined on their reducing powers and saccharide compositions similarly as in Experiment 6. The results were as shown in Table 8.

TABLE 8

| Concentration of maltose (%) | Reaction time (hour) | Reducing power (%) | Saccharide composition (%) | | |
| --- | --- | --- | --- | --- | --- |
| | | | Glucose | Maltose | Trehalose |
| | 0 | 50.3 | 0.0 | 100.0 | 0.0 |
| 5.0 | 2 | 43.8 | 0.8 | 88.0 | 11.2 |
| | 7 | 35.0 | 0.5 | 72.7 | 26.8 |
| | 24 | 17.2 | 0.5 | 41.8 | 57.7 |
| | 48 | 10.3 | 1.8 | 29.7 | 68.5 |
| 10.0 | 2 | 46.8 | 1.2 | 86.5 | 12.3 |
| | 7 | 34.6 | 1.4 | 64.9 | 33.7 |
| | 24 | 16.0 | 2.2 | 36.4 | 61.4 |
| | 48 | 14.8 | 3.7 | 26.5 | 69.8 |
| 20.0 | 2 | 44.9 | 0.7 | 86.6 | 12.7 |
| | 7 | 32.7 | 1.2 | 66.6 | 32.2 |
| | 24 | 21.0 | 2.6 | 35.8 | 61.6 |

TABLE 8-continued

| Concentration of maltose (%) | Reaction time (hour) | Reducing power (%) | Saccharide composition (%) | | |
|---|---|---|---|---|---|
| | | | Glucose | Maltose | Trehalose |
| 30.0 | 48 | 11.2 | 3.9 | 27.0 | 69.1 |
| | 2 | 44.8 | 0.0 | 89.5 | 10.5 |
| | 7 | 38.2 | 0.6 | 72.5 | 26.9 |
| | 24 | 17.8 | 1.8 | 41.8 | 56.4 |
| | 48 | 12.9 | 3.9 | 29.6 | 66.5 |

As is evident from the results in Table 8, the present enzyme formed trehalose from maltose in a yield of about 70% independently on the concentration of maltose as a substrate.

EXPERIMENT 14

Preparation of Trehalose From Maltose

Ten parts by weight of maltose commercialized by Hayashibara Biochemical Laboratories, Inc., Okayama, Japan, was dissolved in 40 parts by weight of water, and the solution was mixed with 2 units/g maltose, d.s.b., of the present purified maltose-trehalose converting enzyme, and subjected to an enzymatic reaction at 35° C. and pH 7.0 for 48 hours, followed by heating the resultant reaction mixture at 100° C. for 10 min to inactivate the remaining enzyme. The reaction mixture, containing about 69% trehalose, d.s.b., was decolored with an activated charcoal, desalted with ion-exchangers in H- and OH-form, and concentrated into an about 78 w/v % solution which was then mixed with 0.1% crystalline trehalose as a seed crystal, d.s.b., followed by allowing it to stand at ambient temperature overnight to effect crystallization. The resultant massecuite was separated into a crystal which was then sprayed and washed with a small amount of water, followed by the recovery of an about 2.3 parts by weight of a high-purity crystalline trehalose with a purity of 99.7%, d.s.b.

EXPERIMENT 15

Production of Enzyme

One hundred ml aliquots of a liquid nutrient culture medium, consisting of 0.5 w/v % polypeptone, 0.1 w/v % yeast extract, 0.07 w/v % sodium nitrate, 0.01 w/v % dipotassium hydrogenphosphate, 0.02 w/v % magnesium sulfate, 0.01 w/v % calcium chloride and water, were adjusted to pH 7.5, placed in 00-ml Erlenmeyer flasks, autoclaved at 120° C. for 20 min to effect sterilization, cooled, and inoculated with a seed culture of *Thermus aquaticus* (ATCC 33923), followed by the culture at 60° C. for 24 hours under stirring conditions of 200 rpm. The resultant cultures were pooled and used as a seed culture.

About 20 L aliquots of a fresh preparation of the same liquid nutrient culture medium as used in the above culture were placed in two 30-L fermenters, sterilized, cooled to 60° C., and inoculated with one v/v % of the seed culture, followed by the culture under stirring and aerobic conditions at 60° C. and a pH of 6.5–8.0 for about 20 hours.

The activity of a maltose-trehalose converting enzyme, accumulated in the resultant culture, was 0.35 units/ml. A portion of the culture was centrifuged to separate cells and a supernatant, and the cells were suspended in 50 mM phosphate buffer (pH 7.0) to give the same volume of that of the portion, followed by assaying the enzyme activities in the cell suspension and the supernatant to reveal 0.33 units/ml and 0.02 units/ml respectively. The enzyme activity was assayed at 60° C.

EXPERIMENT 16

Purification the Enzyme

The culture obtained in Experiment 15 was centrifuged to obtain an about 0.28 kg of wet cells which were then suspended in 10 mM phosphate buffer (pH 7.0). About 1.9 L of the resultant cell suspension was treated with "MODEL US300", an ultrasonic disintegrator commercialized by Nippon Seiki Co., Ltd., Niigata, Japan, to disrupt cells. The resultant mixture was centrifuged at 15,000×g for 30 min to obtain an about 1.8 L supernatant. Ammonium sulfate was added to the supernatant and dissolved therein to give a saturation degree of 0.7, and the solution was allowed to stand at 4° C. for 4 hours, and centrifuged to obtain the resultant sediment.

The sediment was dissolved in 10 mM phosphate buffer (pH 7.0), and the solution was dialyzed against a fresh preparation of the same buffer for 24 hours, and centrifuged to remove insoluble substances. The dialyzed solution, 1,560 ml by volume, was divided into three portions which were respectively subjected to ion-exchange column chromatography using a column packed with 530 ml of "DEAE-TOYOPEARL® 650 GEL", a gel commercialized by Tosoh Corporation, Tokyo, Japan.

The present maltose-trehalose converting enzyme adsorbed on the gel and eluted therefrom with a fresh preparation of the same buffer supplemented with salt. The fractions with the enzyme activity were recovered, dialyzed against a fresh preparation of the same buffer supplemented with one M ammonium sulfate, and subjected to hydrophobic column chromatography using a column packed with 380 ml of "BUTYL-TOYOPEARL® 650 GEL", a hydrophobic gel commercialized by Tosoh Corporation, Tokyo, Japan. The maltose-trehalose converting enzyme adsorbed on the gel was eluted therefrom with a liner gradient of salt ranging from 1 M to 0 M, followed by recovering fractions with the enzyme activity.

The fractions were pooled and subjected to gel filtration column chromatography using a column packed with 380 ml of "TOYOPEARL HW-55S", a gel commercialized by Tosoh Corporation, Tokyo, Japan, followed by recovering the eluted fractions with the enzyme activity.

The fractions were pooled and subjected to ion-exchange chromatography using a column paced with 1.0 ml of 637 MONO Q HR5/5" commercialized by Pharmacia LKB Biotechnology AB, Uppsala, Sweden. The enzyme was eluted from the column with a liner gradient of salt ranging from 0.1M to 0.35 M, followed by recovering fractions with the enzyme activity. The total activity, specific activity and yield in each purification step are tabulated in Table 9.

TABLE 9

| Purification step | Total enzyme* activity (units) | Specific activity (units/ mg protein) | Yield (%) |
| --- | --- | --- | --- |
| Supernatant after cell disruption | 8,800 | 0.10 | 100 |
| Dialyzed solution after salting out | 8,710 | 0.16 | 99.0 |
| Eluate from ion-exchange column | 5,690 | 2.5 | 64.7 |
| Eluate from hydrophobic column | 2,050 | 17.6 | 23.3 |
| Eluate from gel filtration column | 937 | 113 | 10.6 |
| Eluate from ion-exchange column | 467 | 135 | 5.3 |

Note:
The symbol "*" means the present maltose-trehalose converting enzyme.

The purified enzyme preparation was subjected to gel electrophoresis using 5 w/v % sodium dodecylsulfate polyacrylamide gel to show a single protein band. This meant that it was a relatively-high purity preparation. EXPERIMENT 17

Property of Enzyme

A portion of a purified maltose-trehalose converting enzyme preparation, obtained by the method in Experiment 16, was electrophoresed on a gel containing 7.5 w/v % sodium dodecylsulfate polyacrylamide gel, and determined its molecular weight to be about 100,000–110,000 daltons by comparing it with those of marker proteins, commercialized by Japan Bio-Rad Laboratories, Tokyo, Japan, which had been simultaneously electrophoresed.

Another portion of the purified maltose-trehalose converting enzyme preparation was isoelectrophoresed on a polyacrylamide gel containing 2 w/v % "AMPHOLINE", an ampholyte commercialized by Pharmacia LKB Biotechnology AB, Uppsala, Sweden. Thereafter, the resultant gel was sliced into pieces, followed by measuring their pHs to reveal the pI of the enzyme being about 3.8–4.8.

Figure 9:
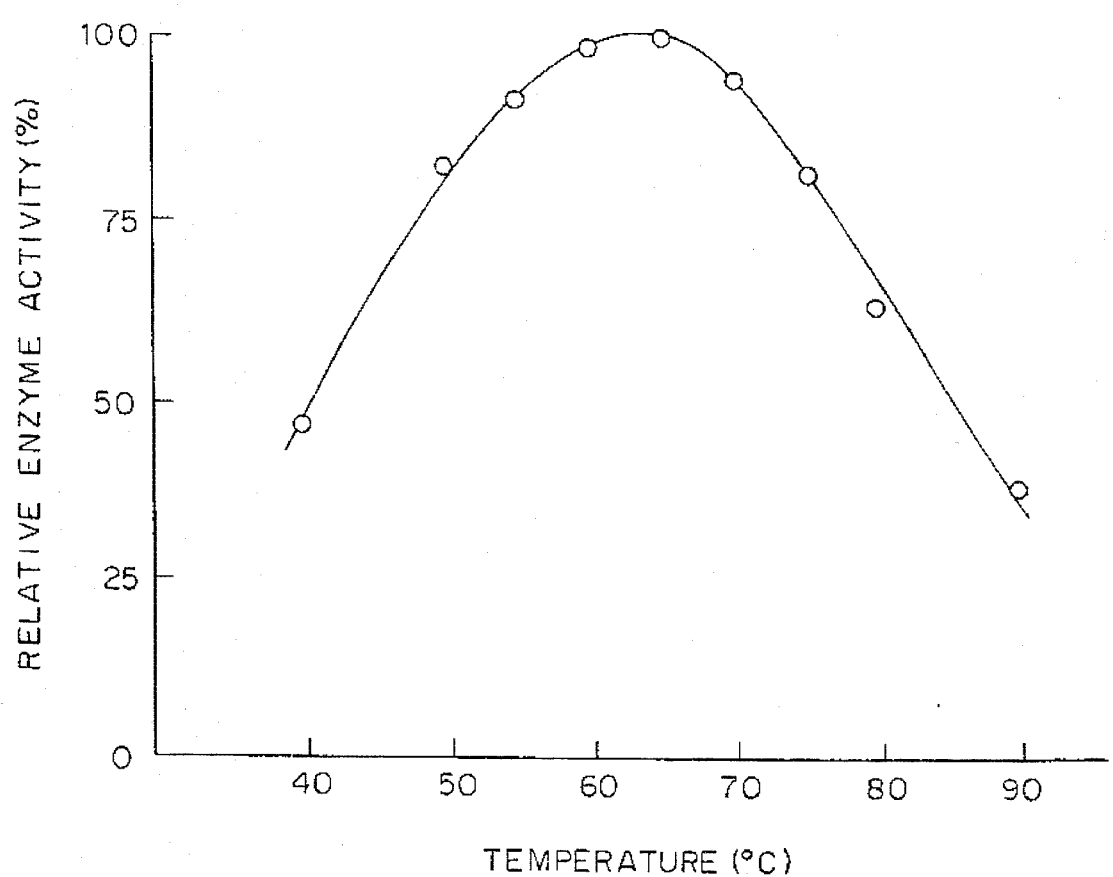
FIG. 9 shows the influence of temperature on the enzyme activity of the present maltose-trehalose converting enzyme derived from *Thermus aquaticus* (ATCC 33923).
Figure 10:
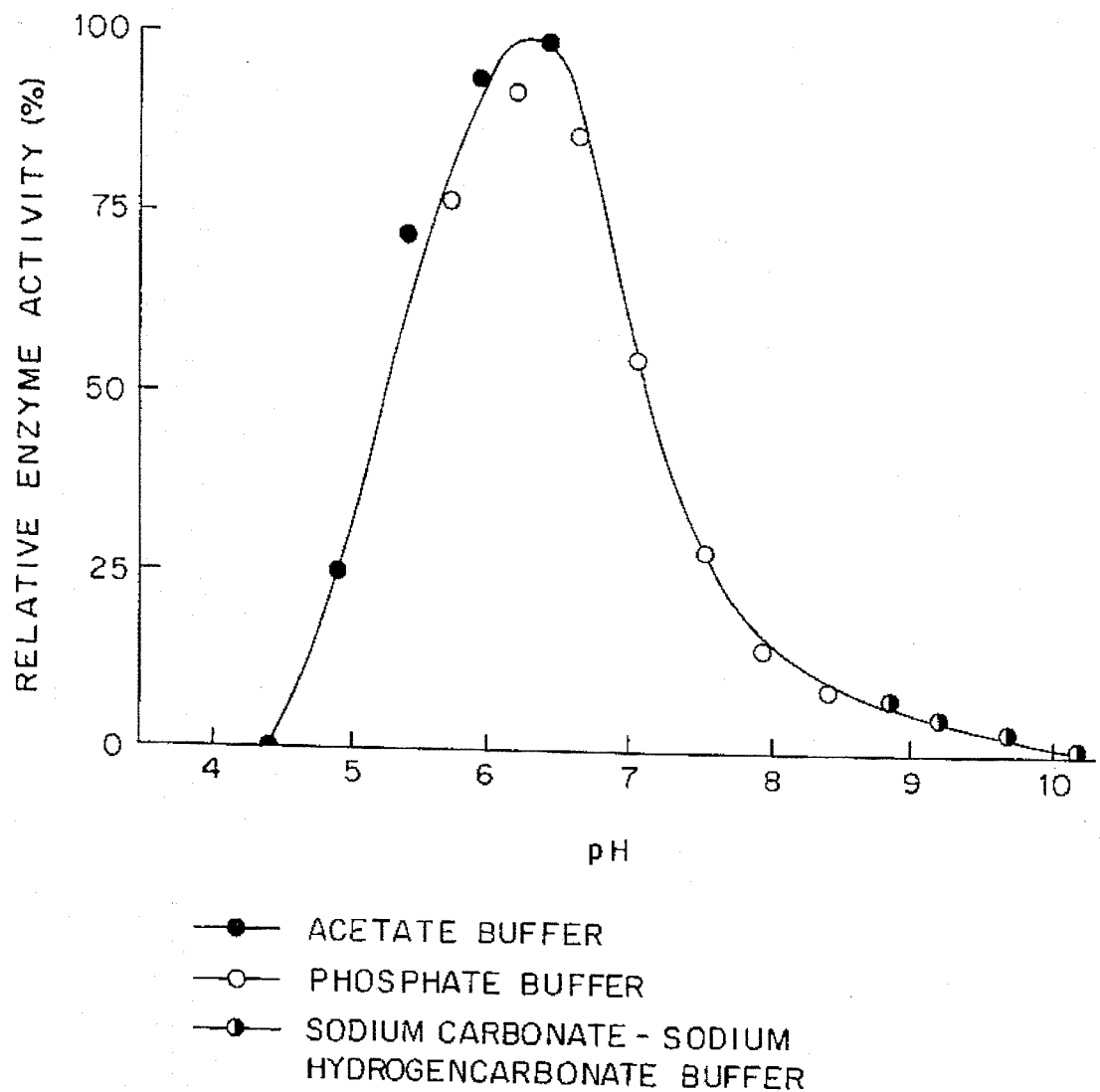
FIG. 10 shows the influence of pH on the enzyme activity of the present maltose-trehalose converting enzyme derived from *Thermus aquaticus* (ATCC 33923).
Figure 11:
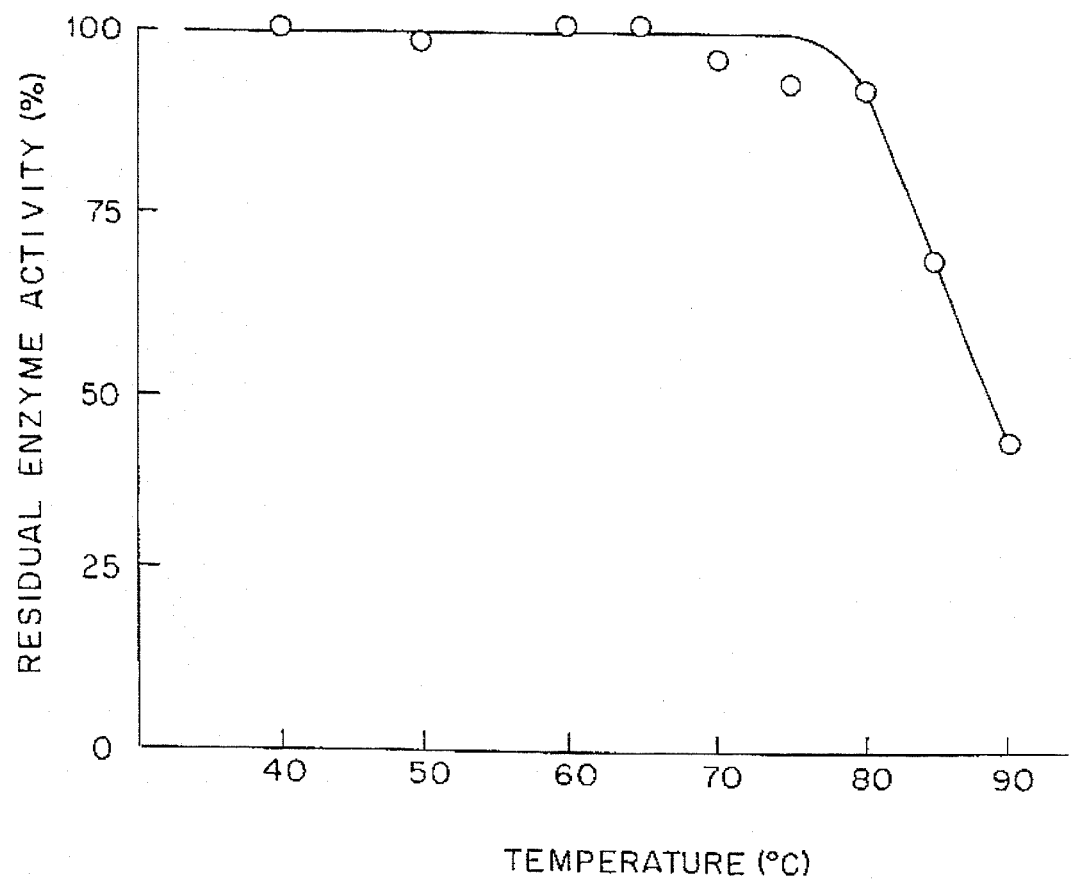
FIG. 11 shows the influence of temperature on the stability of the present maltose-trehalose converting enzyme derived from *Thermus aquaticus* (ATCC 33923).
Figure 12:
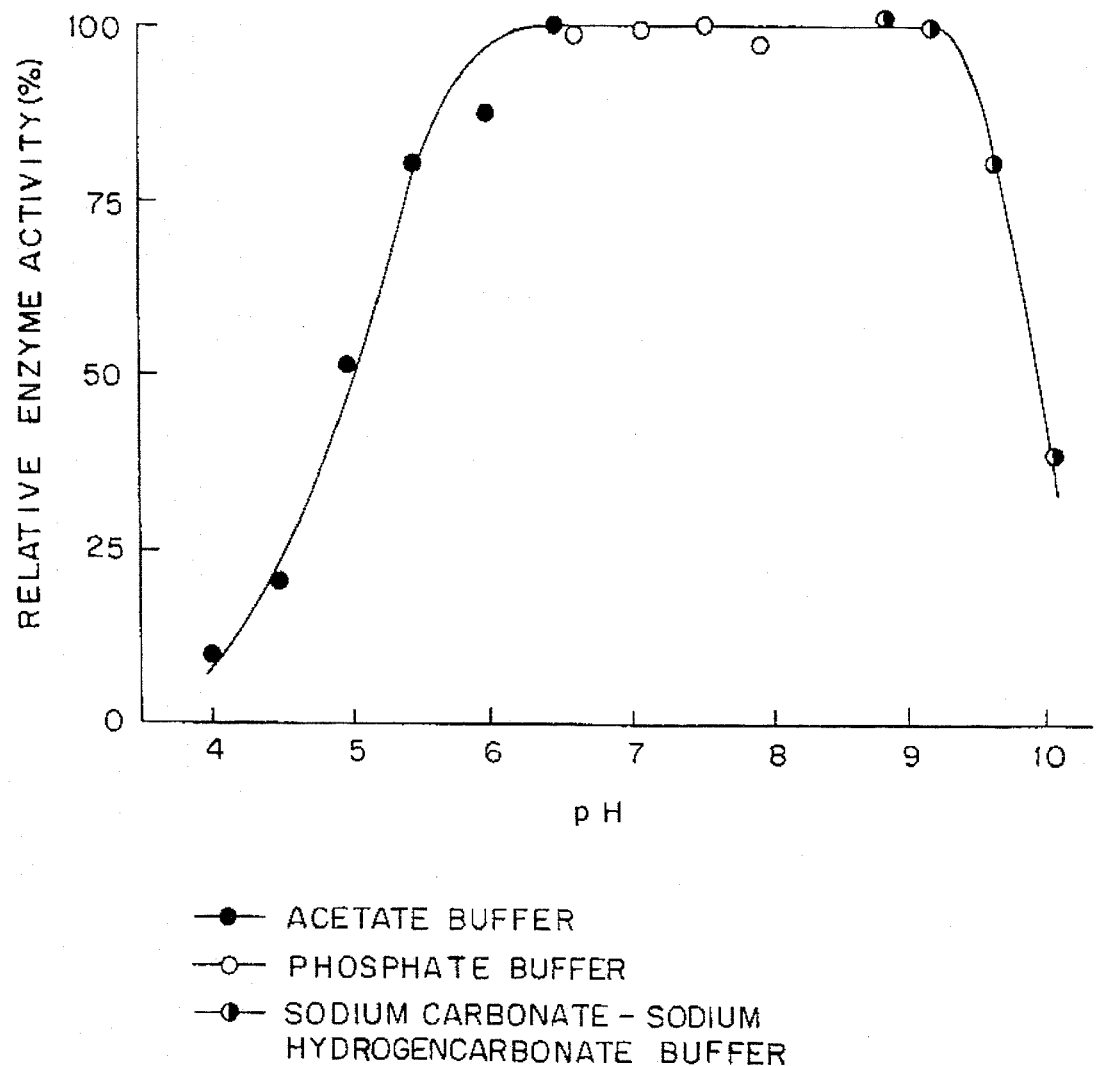
FIG. 12 shows the influence of pH on the stability of the present maltose-trehalose converting enzyme derived from *Thermus aquaticus* (ATCC 33923).

Effects of temperature and pH on the activity of the present enzyme were studied in accordance with the method as used for assaying the enzyme activity. The results were respectively shown in FIG. 9 (effect of temperature) and FIG. 10 (effect of pH). The optimum temperature of the enzyme was about 65° C. when incubated at pH 7.0 for 60 min, and the optimum pH was about 6.0–6.7 when incubated at 60° C. for 60 min. The thermal stability of the enzyme was determined by incubating it in 50 mM phosphate buffers (pH 7.0) in test tubes at different temperatures for 60 min, cooling the test tubes with cold water, and assaying the residual enzyme activity in each buffer. The pH stability of the enzyme was determined by incubating it in 50 mM phosphate buffers having different pHs at 60° C. for 60 min, adjusting the resultant buffers to pH 7.0, and assaying the residual enzyme activity in each buffer. The results of the thermal- and pH-stabilities of the enzyme were respectively shown in FIGS. 11 and 12. The enzyme was stable up to a temperature of about 80° C. and stable at a pH of about 5.5–9.5. One mM $Cu^{++}$ or $Hg^{++}$ and 50 mM Tris-HCl buffer were inhibitory to the present enzyme.

EXPERIMENT 18

Action on Saccharides

A variety of saccharides were tested for determining whether they could be used as a substrate for the present enzyme from *Thermus aquaticus* (ATCC 33923), obtained in accordance with the method in Experiment 4 except for setting the reaction temperature to 50° C. Similarly as the enzymes from Pimelobacter sp. R48 and *Pseudomonas putida* H262, the enzyme from *Thermus aquaticus* (ATCC 33923) specifically acted on maltose and trehalose, i.e., it converted maltose into trehalose and vice versa. It was revealed that the equilibrium position of the conversion reaction inclined to the formation of trehalose, i.e. the conversion rate of maltose into trehalose was about 70% or higher.

EXPERIMENT 19

Influence of Maltose Concentration on the Formation of Trehalose

To a solution containing 2.5, 5, 10, 20 or 40% maltose was added 2.5 units/g maltose, d.s.b., of a purified maltose-trehalose converting enzyme derived from *Thermus aquaticus* (ATCC 33923) obtained by the method in Experiment 16, and the solution was subjected to an enzymatic reaction at 6° C. and pH 6.5. The reaction mixture was sampled at 72 hours after the initiation of the enzymatic reaction, and heated to inactivate the remaining enzyme at 100° C. for 30. The sample was determined on the reducing power and saccharide composition similarly as in Experiment 6. The results were as shown in Table 10.

TABLE 10

| Concentration of maltose (%) | Reaction time (hour) | Reducing power (%) | Saccharide composition (%) | | |
| --- | --- | --- | --- | --- | --- |
| | | | Glucose | Maltose | Trehalose |
| | 0 | 50.3 | 0.0 | 100.0 | 0.0 |
| 2.5 | 72 | 16.3 | 4.5 | 25.2 | 70.3 |
| 5.0 | 72 | 15.9 | 4.4 | 25.6 | 70.0 |
| 10.0 | 72 | 16.0 | 4.7 | 25.6 | 69.7 |
| 20.0 | 72 | 16.6 | 4.4 | 26.2 | 69.4 |
| 40.0 | 72 | 16.8 | 5.0 | 26.4 | 68.6 |

As is evident from the results in Table 10, the present enzyme formed trehalose from maltose in a yield of about 70% independently on the concentration of maltose as a substrate.

EXPERIMENT 20

Influence of Temperature on the Formation of Trehalose

To 20% maltose solution having pH 6.5 was added 2.5 units/g maltose, d.s.b., of a maltose-trehalose converting enzyme derived from *Thermus aquaticus* (ATCC 33923) obtained by the method in Experiment 16, and the mixture was subjected to an enzymatic reaction at 40°, 50° 60° or 70° C. while sampling at a prescribed time interval. The samples were heated at 100° C. for 30 min to inactivate the remaining enzyme. The resultant reaction mixtures were analyzed on their saccharide compositions on HPLC similarly as in Experiment 6. The trehalose content at different temperatures and reaction times were as shown in Table 11.

TABLE 11

| Reaction time | Trehalose content (%) | | | |
|---|---|---|---|---|
| (hour) | 40° C. | 50° C. | 60° C. | 70° C. |
| 4 | 45.0 | 55.7 | 56.8 | 50.3 |
| 8 | 61.0 | 67.3 | 64.3 | 58.5 |
| 24 | 79.1 | 76.5 | 71.1 | 64.3 |
| 48 | 80.7 | 76.9 | 70.2 | 62.8 |
| 72 | 80.0 | 76.4 | 68.5 | 60.2 |

As is evident from the results in Table 11, the lower the enzymatic reaction temperature, the higher the conversion rate of maltose into trehalose. The enzyme converted maltose into trehalose in a conversion rate of about 80%.

EXPERIMENT 21

Production and Property of Maltose-trehalose Converting Enzyme From Microorganism Among conventional microorganisms, a microorganism which had been confirmed its ability to form the present maltose-trehalose converting enzyme was incubated in an Erlenmeyer flask for 48 hours in accordance with Experiment 15. After analyzed the enzyme activity, the resultant culture was subjected to a cell disrupting apparatus in accordance with Experiment 16. From the resultant mixture a supernatant was prepared and dialyzed to obtain a partially purified enzyme, followed by analyzing the property in accordance with Experiment 17. The results were as shown in Table 12.

TABLE 12

| Microorganism | Activity (unit/ml) | Optimum temperature (°C.) | Optimum pH | Thermal stability (°C.) | pH Stability |
|---|---|---|---|---|---|
| *Thermus aquaticus* (ATCC 27634) | 0.30 | About 65 | About 6.0–6.5 | up to 80 | About 5.5–9.5 |
| *Thermus ruber* (ATCC 35948) | 0.26 | About 50 | About 6.0–7.0 | up to 50 | About 5.5–10.0 |
| Thermus sp. (ATCC 43815) | 0.25 | About 65 | About 6.0–6.5 | Up to 80 | About 5.5–9.5 |
| Pimelobacter sp. (ATCC 43815) described in Experiments 1–3 | 0.55 | About 20 | About 7.0–8.0 | Up to 30 | About 6.0–9.0 |
| *Pseudomonas putida* described in Experiments 12–14 | 0.12 | About 37 | About 7.3–8.3 | Up to 40 | About 6.0–9.5 |
| *Thermus aquaticus* (ATCC 33923) described in Experiments 18–20 | 0.35 | About 65 | About 6.0–6.7 | up to 80 | About 5.5–9.5 |

Partially purified enzymes derived from known microorganisms of the genus Thermus as shown in Table 12 were studied on their action on a variety of saccharides in accordance with the method in Experiment 18. As a result, it was revealed that similarly as the enzyme derived from *Thermus aquaticus* (ATCC 33923) the partially purified enzymes specifically acted on maltose and trehalose, and formed trehalose from maltose.

It was revealed that the maltose-trehalose converting enzyme derived from *Thermus ruber* (ATCC 35948) showed a lower optimum temperature and a lower stable temperature than that of *Thermus aquaticus* (ATCC 33923), while the enzymes derived from microorganisms of the genus Thermus had approximately the same property of that of *Thermus aquaticus* (ATCC 33923) as well as having a relatively-high thermal stability.

EXPERIMENT 22

Partial Amino Acid Sequence of Maltose-trehalose Converting Enzyme

A portion of a purified enzyme preparation derived from Pimelobacter sp. R48 obtained by the method in Experiment 2, *Pseudomonas putida* H262 obtained by the method in Experiment 10, or *Thermus aquaticus* (ATCC 33923) obtained by the method in Experiment 16 was dialyzed against distilled water, and an about 80 µg protein of the resultant was used as a sample for analyzing a partial amino acid sequence containing the N-terminal of the enzyme. The N-terminal was analyzed on 637 PROTEIN SEQUENCER MODEL 473A", a protein sequencer commercialized by Applied Biosystems Inc., Foster City, USA. The partial amino acid sequence containing the N-terminal of each enzyme was as shown in Table 13.

TABLE 13

| Microorganism | Partial amino acid sequence containing the N-terminal |
|---|---|
| *Pseudomonas putida* H262 | Gly—Lys—Trp—Pro—Arg—Pro—Ala—Ala—Phe—Ile—<br>1　　　　　　　　5　　　　　　　　　　10<br>Asp (SEQ ID NO: 1) |
| *Pimelobacter* sp. R48 | Ser—Thr—Val—Leu—Gly—Glu—Glu—Pro—Glu—Trp—<br>1　　　　　5　　　　　　　　　10<br>Phe—Arg—Thr—Ala—Val—Phe—Tyr—Glu<br>　　　　　　　　15<br>(SEQ ID NO: 2) |
| *Thermus aquaticus* ATCC 33923 | Met—Asp—Pro—Leu—Trp—Tyr—Lys—Asp—Ala—Val—<br>1　　　　　　　　5　　　　　　　　　　10<br>Ile—Try—Gln (SEQ ID NO 3) |

Note:
In the Table, each figure means the number of amino acids counted from the N-terminal of each partial amino acid sequence.

As is evident from the results in Table 13, it was revealed that the enzymes derived from Pimelobacter sp. R48, *Pseudomonas putida* H262 and *Thermus aquaticus* (ATCC 33923) had partial amino acid sequences which were highly homologous. A relatively-high homology was found between a partial amino acid sequence ranging from the 10th amino acid of "Trp" to the 16th amino acid of "Phe" derived from a microorganism of the genus Pimelobacter and that ranging from the 3rd amino acid of "Trp" to the 9th amino acid of "Phe" derived from a microorganism of the genus Pseudomonas. The partial amino acid sequence can be expressed by Trp-$X_1$-Arg-$X_2$-Ala-$X_3$-Phe (SEQ ID NO: 4) (where the symbol "$X_1$" means "Phe" or "Pro"; the symbol "$X_2$", "Thr" or "Pro"); and the symbol "$X_3$", "Val" or "Ala"). A relatively-high homology was found between a partial amino acid sequence ranging from the 14th amino acid of "Ala" to the 17th amino acid of "Tyr" derived from a microorganism of the genus Pimelobacter and that ranging from the 9th amino acid of "Ala" to the 12th amino acid of "Tyr" derived from a microorganism of the genus Thermus. The partial amino acid sequence can be expressed by Ala-Val-$X_4$-Tyr (SEQ ID NO: 5) (where the symbol "$X_4$" means "Phe" or "Ile").

EXPERIMENT 23

Physicochemical Property of Trehalose

A high-purity trehalose specimen prepared by the method in Experiment 8 was studied on its physicochemical property. As a result, the melting point was determined as 97.0° C., the specific rotation was $[\alpha]_D^{20}$+199° C. (c=5), the heat of fusion was 57.8 kJ/mole, and the solubility in water at 25° C. was 77.0 g for anhydrous trehalose. These data well agreed with those of a commercially available hydrous crystalline trehalose purchased from Wako Pure Chemical Industries, Ltd., Tokyo, Japan, which had been experimented along with the above experiments.

EXPERIMENT 24

Utilization Test in Vivo

In accordance with the method as reported by H. Atsuji et al. in *Journal of Clinical Nutrition*, Vol.41, No. 2, pp.200–208 (1972), 30 g of the high-purity trehalose specimen with a purity of 99.8%, d.s.b., in Experiment 8 was prepared into a 20 w/v % aqueous solution which was then orally administered to 3 healthy male volunteers of 26-, 27- and 30-year-old, and their bloods were sampled at pre- scribed time intervals, followed by the measurements of the blood sugar- and insulin-levels. As a control glucose was used. As a result, trehalose behaved similarly as glucose, and the maxima of blood sugar- and insulin-levels were observed at an about 0.5–1 hour after the administration. This revealed that the present trehalose is readily digested, absorbed and metabolized by living bodies and utilized as an energy source. Thus, the present trehalose and saccharide composition containing the same are suitably used as an energy-supplementing saccharide.

EXPERIMENT 25

Acute Toxicity Test

By using mice, the high-purity trehalose specimen with a purity of 99.8%, d.s.b., prepared in Experiment 8 was orally administered to the mice for its acute toxicity test. The result revealed that the present trehalose is a relatively-low toxic substance, and no mouse died even when administered with the highest level of dose administrable to the mice. Though it is not so accurate, the $LD_{50}$ was determined to be 50 g/kg or higher.

The present trehalose and saccharide composition containing the same, prepared with the present maltose-trehalose converting enzyme, as well as their preparations, are illustrated in Example A. The present compositions containing either the trehalose or the saccharide composition containing the same are illustrated in Example B:

EXAMPLE A-1

In accordance with the method in Experiment 1, a seed culture of a microorganism of the species Pimelobacter sp. R48 (FERM BP-4315) was cultured by a fermenter for about 60 hours under aeration and agitation conditions in a fresh preparation of the same nutrient culture medium as used in Experiment 1 except for adjusting the glucose concentration to 4.0 w/v %. The activity of the present maltose-trehalose converting enzyme in the resultant culture was 0.75 units/ml. A portion of the culture was centrifugally separated into cells and a culture supernatant which were then assayed their enzyme activity. As a result, about 65% of the enzyme activity was observed in the cells and about 35% of the enzyme activity was observed in the culture supernatant. An about 35 L culture containing cells was treated with "MINI-RABO", a supper high-pressure cell disrupting apparatus commercialized by Dainippon Pharmaceutical Co., Ltd., Tokyo, Japan, to disrupt the cells. The resultant cell suspension was centrifuged to obtain a supernatant which was then membrane filtered with a UF-membrane, followed by recovering an about 1.2 L concentrate containing about 15 units/ml of the present maltose-trehalose converting enzyme.

To a 10 w/v % suspension (pH 5.5) of potato starch was added 2 units/g starch, d.s.b., of "SPITASE HS", an α-amylase specimen commercialized by Nagase Biochemicals Ltd., Kyoto, Japan, and the resultant mixture was gelatinized and liquefied under stirring and heating conditions, followed by immediately keeping the mixture at 120° C. for 20 min and adjusting the resultant to 50° C. and pH 5.0. The mixture thus obtained was mixed with 20 units/g starch, d.s.b., of a β-amylase specimen commercialized by Nagase Biochemicals Ltd., Kyoto, Japan, and 500 units/g starch, d.s.b., of an isoamylase specimen commercialized by Hayashibara Biochemical Laboratories, Inc., Okayama, Japan, and the resultant mixture was subjected to an enzymatic reaction for 24 hours to obtain a saccharide solution containing about 92 w/v % maltose. The reaction mixture was heated at 100° C. for 20 min, heated to 10° C., adjusted to pH 7.0, mixed with one unit/g dry matter of the maltose-trehalose converting enzyme prepared in the above, and subjected to an enzymatic reaction for 96 hours.

The reaction mixture was kept at 95° C. for 10 min, cooled, decolored and filtered in usual manner with an activated charcoal. The filtrate was purified by desalting it with ion exchangers in H- and OH-form, and concentrated to obtain a syrup with a concentration of about 70 w/v % in a yield of about 95%, d.s.b.

The product, containing about 69% trehalose, d.s.b., and having a reducing power as low as DE 18.2, has a mild sweetness as well as an appropriate viscosity and moisture-retaining ability, and because of these it is suitably used as a sweetener, taste-improving agent, stabilizer, diluent, excipient and filler in a variety of compositions such as food products, cosmetics and pharmaceuticals.

EXAMPLE A-2

A reaction mixture, wherein an enzymatic reaction of a maltose-trehalose conversion had been suspended, was prepared by the method in Example A-1, mixed with 10 units/g "GLUCOZYME", a glucoamylase commercialized by Nagase Biochemicals, Ltd., Kyoto, Japan, and subjected to an enzymatic reaction at pH 5.0 and 50° C. for 24 hours. The resultant reaction mixture was heated to inactivate the remaining enzyme, decolored, desalted and purified to obtain a saccharide solution as a feed solution. The saccharide solution was subjected to ion-exchange column chromatography using "XT-1016 ($Na^+$-form, polymerization degree of 4%)" commercialized by Tokyo Organic Chemical Industries, Ltd., Tokyo, Japan. The resins were packed in 4-jacketed stainless-steel columns, having an inner diameter of 5.4 cm, cascaded in series to give a total gel-bed-depth of 20 m.

While keeping the inner column temperature at 60° C., the saccharide solution was fed to the columns in an amount of 5 v/v %, fractionated by feeding to the columns 60° C. hot water at SV (space velocity) 0.15 to remove glucose, followed by recovering a high trehalose content fractions. The fractions were pooled, purified, concentrated, dried in vacuo and pulverized to obtain a high trehalose content powder in a yield of about 55%, d.s.b.

The product, containing about 97% trehalose, d.s.b., and having a satisfactorily-low reducing power as well as a mild and high-quality sweetness, can be arbitrarily used as a sweetener, taste-improving agent, quality-improving agent, stabilizer, diluent, excipient and filler in a variety of compositions such as food products, cosmetics and pharmaceuticals.

EXAMPLE A-3

A high trehalose content fraction obtained by the method in Example A-2 was in usual manner decolored with an activated charcoal, desalted and purified with an ion-exchanger. The filtrate was concentrated into an about 70 w/v % solution which was then placed in a crystallizer, admixed with about 2% hydrous crystalline trehalose as a seed crystal, and gradually cooled to obtain a massecuite with a crystallinity of about 45%. The massecuite was sprayed from a nozzle equipped at the top of a drying tower at a high pressure of 150 kg/cm². In the spraying step, the massecuite was simultaneously ventilated with 85° C. hot air being sent from the top of the drying tower, and the resultant crystalline powder was collected on a metal wire netting conveyer provided on the basement of the drying tower, and gradually moved out from the drying tower while a stream of 45° C. air was passing upwards through the metal wire netting. The resultant crystalline powder was injected in an ageing tower and aged for 10 hours to complete the crystallization and drying, followed by recovering the resultant hydrous crystalline trehalose powder in a yield of about 90% against the material high trehalose content fraction, d.s.b.

The product is substantially non-hygroscopic and handles easily, and these render it arbitrarily useful in a variety of compositions such as food products, cosmetics and pharmaceuticals as a sweetener, taste-improving agent, quality-improving agent and stabilizer.

EXAMPLE A-4

A high trehalose content fraction obtained by the method in Example A-2 was purified similarly as in Example A-3, and the resultant was placed in an evaporator, and boiled up in vacuo to obtain a syrup with a moisture content of about 3.0%. The resultant syrup was placed in a crystallizer, admixed with one % anhydrous crystalline trehalose against the syrup, d.s.b., and crystallized at 120° C. under stirring conditions, and the resultant mixture was placed in a aluminum plain container and aged at 100° C. for 6 hours to form a block.

The resultant block was pulverized by a cutter and dried by a fluidized-bed drying to obtain an anhydrous crystalline trehalose powder with a moisture content of about 0.3% in a yield of about 85% against the material high trehalose content fraction, d.s.b.

The product can be arbitrarily used as a desiccant in food products, cosmetics, pharmaceuticals, and their materials and intermediates, and also can be used as a white powdery sweetener in a variety of compositions such as food products, cosmetics and pharmaceuticals.

EXAMPLE A-5

In accordance with the method in Experiment 1, a seed culture of Pimelobacter sp. R48 (FERM BP-4315) was inoculated to and cultured in a nutrient culture medium, and the resultant culture was centrifuged to obtain 100 g wet cells, having an activity of about 800 units of the present enzyme, which were then kneaded with 100 ml of 10 mM phosphate buffer in which 2.5% sodium alginate, having a viscosity of 300–400 cp, commercialized by Wako Pure Chemical Industries, Ltd., Tokyo, Japan, was previously dissolved in 10 mM phosphate buffer. The resultant slurry containing the cells was successively dropped into 0.1 M calcium chloride solution stirred by a magnetic stirrer from a height of about 20 cm above the surface of the solution to form spherical gels having a diameter of about 2 mm. The gels were allowed to stand in the solution at ambient temperature for about 2 hours and filtered with a Buchner funnel, followed by recovering cells immobilized with alginate. The resultant immobilized cells were packed in a jacketed glass-column, 30 mm in diameter and 200 mm in length, and the column was heated and kept at 20° C. A 40% maltose solution (pH 6.8) was fed to the column at SV 0.2 to flow it downward to obtain a saccharide solution containing about 70% trehalose, d.s.b. The saccharide solution thus obtained was purified and concentrated to obtain a syrup with a concentration of about 70% in a yield of about 95%, d.s.b.

The product has a relatively-low reducing power and a mild sweetness as well as an appropriate moisture-retaining ability, and because of these it can be arbitrarily used in a variety of compositions similarly as the product in Example A-1.

EXAMPLE A-6

A 33% corn starch suspension was mixed with calcium carbonate to give a final concentration of 0.1%, and the mixture was adjusted to pH 6.5 which was then mixed with 0.2 units/g starch, d.s.b., of "TERMAMYL 60L", an α-amylase specimen commercialized by Novo Industri A/S Copenhagen Denmark, and subjected to an enzymatic reaction at 95° C. for 15 min. The reaction mixture was autoclaved at 120° C. for 30 min, cooled to 55° C., admixed with 500 units/g starch, d.s.b., of an isoamylase specimen commercialized by Hayashibara Biochemical Laboratories, Inc., Okayama, Japan, and 30 units/g starch, d.s.b., of a β-amylase specimen commercialized by Nagase Biochemicals Ltd., Kyoto, Japan, and subjected to an enzymatic reaction for 48 hours, followed by recovering a saccharide solution with a maltose content of about 84%, d.s.b. The saccharide solution was kept at 100° C. for 10 min, cooled to 15° C., mixed with 1.5 units/g starch, d.s.b., of the present maltose-trehalose converting enzyme obtained by the method in Example A-1, and subjected to an enzymatic reaction for 72 hours. The resultant reaction mixture was heated at 100° C. for 15 min to inactivate the remaining enzyme and decolored in usual manner with an activated charcoal, desalted and purified with an ion-exchanger, followed by concentrating the resultant to obtain a syrup with a concentration of about 70% in a yield of about 95%, d.s.b.

The product contains about 64% trehalose, d.s.b., and has a relatively-low reducing power and a mild sweetness as well as an appropriate moisture-retaining ability, and because of these it can be arbitrarily used in a variety of compositions similarly as the product in Example A-1.

EXAMPLE A-7

A syrup obtained by the method in Example A-5 was concentrated into an about 82% syrup which was then placed in a crystallizer, admixed with an about one % seed crystal, transferred to a plain vessel, and allowed to stand at 20° C. for 4 days to effect crystallization. The resultant crystal was pulverized by a cutter and dried to obtain a massecuite-type hydrous crystalline trehalose powder in a yield of about 95%, d.s.b.

The product does not substantially exhibit hygroscopicity and handles easily, and because of these it can be arbitrarily used similarly as the product in Example A-1 in a variety of compositions.

EXAMPLE A-8

A syrup obtained by the method in Example A-6 was concentrated into an about 80% syrup which was then placed in a crystallizer, admixed with an about one % of hydrous crystalline trehalose as a seed crystal, and cooled under stirring conditions to effect crystallization. The resultant was separated with a basket-type centrifuge to obtain a crystal which was then sprayed with a small amount of cold water to obtain a high-purity hydrous crystalline trehalose in a yield of about 20%, d.s.b.

The product which exhibits the same physicochemical properties as shown in Experiment 23 can be arbitrarily used as a sweetener, taste-improving agent, quality-improving agent, stabilizer in a variety of compositions such as food products, cosmetics and pharmaceuticals, as well as industrial reagents and chemical materials.

EXAMPLE A-9

A seed culture of *Pseudomonas putida* H262 (FERM BP-4579) was inoculated in a nutrient culture medium, and, in accordance with the method in Experiment 9, fermented by a fermentor for about 20 hours under stirring and aerobic conditions. An about 18 L of the resultant culture was centrifuged to obtain an about 0.4 kg wet cells which were then suspended in 4 L of 10 mM phosphate buffer, treated with "MODEL US300", an ultrasonic disintegrator commercialized by Nippon Seiki Co., Ltd., Niigata, Japan, to disrupt cells. The resultant mixture was centrifuged to obtain a supernatant which was then concentrated with a UF-membrane, followed by recovering an about 400 ml of a concentrated enzyme solution containing 3.8 units/ml of a maltose-trehalose converting enzyme. Ten % potato suspension (pH 5.5) was mixed with 2 units/g starch, d.s.b., of "SPITASE HS", an α-amylase specimen commercialized by Nagase Biochemicals, Ltd., Kyoto, Japan, gelatinized and liquefied by heating under stirring conditions, followed by autoclaving at 120° C. for 20 min, cooling to 50° C. and adjusting to pH 5.5. To the resultant mixture was added 500 units/g starch, d.s.b., of a pullulanase specimen commercialized by Hayashibara Biochemical Laboratories, Inc., Okayama, Japan, and 20 units/g starch, d.s.b., of a β-amylase specimen commercialized by Nagase Biochemicals, Ltd., Kyoto, Japan, and subjected to an enzymatic reaction for 24 hours, followed by recovering a saccharide solution containing about 92% maltose. The saccharide solution was heated at 100° C. for 20 min, adjusted to 40° C. and pH 7.0, mixed with 1.5 units/g of the maltose-trehalose converting enzyme prepared in the above, and subjected to an enzymatic reaction for 72 hours. The reaction mixture was heated at 95° C. for 10 min, cooled, and, in usual manner, decolored and filtered with an activate charcoal, followed by desalting and purifying the resultant with ion-exchangers in H- and OH-form, and concentrating the resultant solution to obtain a syrup with a concentration of about 70 w/v % in a yield of about 97%, d.s.b. The product contained about 65% trehalose, d.s.b., and had a relatively-low reducing power as low as DE 16.2, as well as having a moderate sweetness and an adequate viscosity and moisture-retaining ability, and because of these it can be arbitrarily used as a sweetener, taste-improving agent, stabilizer, filler, diluent and excipient

EXAMPLE A-10

A post-reaction mixture of maltose-trehalose converting enzyme obtained by the method in Example A-9 was heated at 95° C. for 10 min to inactivate the remaining enzyme, adjusted to pH 5.0 and 55° C., mixed with 10 units/g starch, d.s.b., of "GLUCOZYME", a glucoamylase specimen commercialized by Nagase Biochemicals, Ltd., Kyoto, Japan, and subjected to an enzymatic reaction for 24 hours. The reaction mixture was in usual manner heated to inactivate the remaining enzyme, decolored, desalted, purified, concentrated into a 55% saccharide solution. Similarly as in Example A-2, the resultant saccharide solution was subjected to column chromatography using "DOWEX 99 ($Ca^{++}$-form, polymerization degree of 6%)", an alkaline-earth metal strong-acid cation exchanger commercialized by Dow Chemical Co., Midland, Mich., USA, followed by recovering high trehalose content fractions. The fractions were pooled, purified and continuously crystallized while concentrating, and the resultant massecuite was separated by a basket-type centrifuge, followed by spraying the resultant crystal with a small amount of water to obtain a high purity hydrous crystalline trehalose in a yield of about 25%, d.s.b. The product exhibits the same physicochemical properties as the product in Experiment 23, and, similarly as the product in Example A-8, it can be arbitrarily used in a variety of compositions such as food products, cosmetics and pharmaceuticals, as well as industrial reagents and chemical materials.

EXAMPLE A-11

A seed culture of *Pseudomonas putida* H262 (FERM BP-4579) was culture in a nutrient culture medium similarly as in Experiment 9, and the resultant cells were recovered by centrifugation to obtain 100 g wet cells having a maltose-trehalose converting enzyme activity of about 400 units which were then kneaded with 100 ml of 10 mM phosphate buffer in which 2.5% sodium alginate having a viscosity of 300–400 cp had been dissolved. The slurry containing the cells were continuously dropped into 0.1 M $CaCl_2$ solution stirred by a magnetic stirrer from a height of about 20 cm above the surface of the solution to form spherical gels having a diameter of about 2 mm. The gels were kept in the $CaCl_2$ solution at ambient temperature for about 2 hours, filtered with a Buchner funnel to obtain cells immobilized with sodium alginate. The immobilized cells were packed in a jacketed glass-column having a diameter of 30 mm and a length of 200 mm and kept at 35° C. The column was fed with a downstream of 40% maltose solution (pH 6.8) at SV 0.1 to obtain a 67% trehalose solution. In accordance with the method in Example A-9, the trehalose solution was purified, concentrated, crystallized, and spray dried to obtain a massecuite-type hydrous crystalline trehalose powder in a yield of about 90%, d.s.b. The product has a relatively-low reducing power, a mild sweetness and an adequate moisture-retaining ability, and because of these it can be arbitrarily used as a variety of compositions similarly as the product in Example A-9.

EXAMPLE A-12

A seed culture of *Thermus aquaticus* (ATCC 33923) was inoculated in a nutrient culture medium, and, in accordance with the method in Experiment 15, cultured for about 20 hours under agitation-aeration conditions. The culture had an activity of about 0.32 units/ml of a maltose-trehalose converting enzyme. 0.18 kg wet cells recovered from an about 18 L of the culture were suspended in 10 mM phosphate buffer (pH 7.0). An about 1.5 L of the cell suspension was treated with an ultrasonic disintegrator to disrupt the cells. The resultant cell debris was centrifuged, and the supernatant was recovered which was then concentrated with a UF-membrane to obtain an about 500 ml concentrate having an activity of about 10 units/ml of a maltose-trehalose converting enzyme. To 15% corn starch suspension (pH 5.5) was added 2 units/g starch of "SPITASE HS", an α-amylase specimen commercialized by Nagase Biochemicals, Ltd., Kyoto, Japan, and gelatinized and liquefied under stirring and heating conditions. Immediately after that the mixture was autoclaved at 120° C. for 20 min, cooled to 55° C. and adjusted to pH 5.0. To the resultant mixture was added 300 units/g starch of a isoamylase specimen commercialized by Hayashibara Biochemical Laboratories, Inc., Okayama, Japan, and 20 units/g starch of a β-amylase specimen commercialized by Nagase Biochemicals, Kyoto, Japan, and subjected to an enzymatic reaction for 24 hours to obtain an about 92% maltose solution. The resultant solution was heated at 100° C. for 20 min, cooled to 50° C., adjusted to pH 7.0, mixed with the maltose-trehalose converting enzyme prepared in the above in an amount of 1.5 units/g dry weight, and subjected to an enzymatic reaction for 72 hours. Thereafter, the resultant culture was heated at 95° C. for 10 min, cooled, and, in usual manner, decolored and filtered with an activate charcoal, followed by desalting and purifying the resultant solution with ion exchangers in H- and OH-form. The resultant solution was concentrated to obtain a 70% syrup in a yield of about 95%, d.s.b. The product contains about 64% trehalose, d.s.b., and has a low reducing power of DE 18.0, as well as having a mild sweetness, adequate viscosity and satisfactory moisture-retaining ability. Because of these it can be arbitrarily used as a sweetener, taste-improving agent, stabilizer, filler, diluent and excipient in a variety of compositions such as food products, cosmetics and pharmaceuticals.

EXAMPLE A-13

A syrup obtained by the method in Example A-12 was concentrated into an about 80% syrup which was then placed in a crystallizer, and, similarly as in Example A-8, crystallized and separated to obtain a high-purity hydrous crystalline trehalose in a yield of about 20%, d.s.b. The product exhibits the same physicochemical properties similarly as the product in Experiment 23, and can be arbitrarily used similarly as the product in Example A-8 as an industrial reagent, industrial material and chemical material in a variety of compositions such as food products, cosmetics and pharmaceuticals.

EXAMPLE A-14

A seed culture of *Thermus aquaticus* (ATCC 33923) was inoculated in a nutrient culture medium, and cultured similarly as the method in Experiment 15, followed by centrifuging the resultant culture to obtain 50 g wet cells having about 1,500 units of a maltose-trehalose converting enzyme activity. The cells were suspended in 100 ml of 2.5% sodium alginate having a viscosity of 300–400 cp, a reagent commercialized by Wako Pure Chemical Industries, Ltd., Tokyo, Japan. The resultant slurry was continuously dropped into 0.1M $CaCl_2$ solution, which was stirring by a magnetic stirrer, from the height of about 20 cm above the surface of the solution to form spherical gels having a diameter of about 2 mm. The gels were allowed to stand in the solution at ambient temperature for about 2 hours, then filtered with a Buchner funnel to obtain cells immobilized with alginate. The immobilized cells were packed in a jacketed-glass column, a diameter of 30 mm and a length of 200 mm, and heated to 60° C. The column was fed with a downstream of 40% maltose solution (pH 6.5) at SV 0.2 to obtain an about 66% trehalose solution which was then in usual manner purified, concentrated and spray dried to obtain a powder trehalose in a yield of about 90%, d.s.b. The powder has a relatively-low reducing power and a mild sweetness, and, similarly as the product in Example A-12, this renders it arbitrarily useful in a variety of compositions such as food products, cosmetics and pharmaceuticals.

EXAMPLE B-1

Sweetener

To one part by weight of a hydrous crystalline trehalose powder, obtained by the method in Example A-8, were homogeneously added 0.01 part by weight of "αG SWEET", an α-glycosyl stevioside product commercialized by Toyo Sugar Refining Co., Ltd., Tokyo, Japan, and 0.01 part by weight of "ASPARTAME", a product of L-aspartyl-L-phenylalanine methylester commercialized by Ajinomoto Co., Ltd., Tokyo, Japan, and the resultant mixture was fed to a granulator to obtain a granular sweetener.

The product has a satisfactory sweetness and an about 2.5-fold higher sweetening power of sucrose, as well as having a caloric value as low as about ⅖ of that of sucrose.

Since the product has a satisfactory stability and does not decompose other sweeteners to be mixed, it can be suitably used as a low-caloric sweetener for low-caloric food products for fat persons and diabetics who are restricted to a reduced calorie intake.

The product does not substantially form acids and insoluble glucans when dental carries-inducing microorganisms act on it, and this renders it useful for sweetening food products to prevent dental carries.

EXAMPLE B-2

Hard candy

One hundred parts by weight of 55 w/v % sucrose solution was mixed by heating with 30 parts by weight of a trehalose syrup, obtained by the method in Example A-1, and the resultant solution was concentrated in vacuo until the moisture content lowered to below 2%. The concentrate was admixed with one part by weight of citric acid and adequate amounts of a lemon flavor and a coloring agent, and the resultant mixture was in usual manner formed into the desired product.

The product is a high-quality hard candy having a satisfactory taste and biting property, as well as having no fear of causing crystallization of sucrose.

EXAMPLE B-3

Chewing Gum

Three parts by weight of a gum base was melted by heating until it softened, and the resultant was mixed with 3 parts by weight of crystalline maltitol and 4 parts by weight of a hydrous crystalline trehalose powder obtained by the method in Example A-3, and further mixed with adequate amounts of a flavor and a coloring agent. The resultant mixture was in usual manner kneaded by a roll, formed and packed to obtain the desired product.

The product is a chewing gum having a satisfactory texture and taste, and suitably used as a relatively-low or substantially no dental carries-inducing chewing gum.

EXAMPLE B-4

Powdered Juice

Thirty-three parts by weight of a powdered orange juice prepared by spray drying was mixed to homogeneity with 50 parts by weight of a massecuite-type high trehalose content powder obtained by the method in Example A-7, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized and granulated with a fluidized-bed granulator for 30 min to obtain granules while being sprayed with as a binder a trehalose syrup obtained by the method in Example A-6, and ventilated with 40° C. air at a flow rate of 150 m$^3$. The granules thus obtained were weighed and packed to obtain the desired product.

The product containing 30% orange juice, d.s.b., retained its high quality for a relatively-long period of time without giving an unsatisfactory taste and smell.

EXAMPLE B-5

Beverage of Lactic Acid Bacteria

One hundred and seventy-five parts by weight of defatted milk powder, 130 parts by weight of a trehalose syrup obtained by the method in Example A-9, 50 parts by weight of a high lactosucrose powder disclosed in Japanese Patent Laid-Open No.281795/92 were dissolved in 1,150 parts by weight of water, and the solution was sterilized by heating it at 65° C. for 30 min, cooled to 40° C., mixed in usual manner with 30 parts by weight of lactic acid bacteria as a starter, and incubate at 37° C. for 8 hours to obtain the desired product with a satisfactory taste and flavor. Since the product contains oligosaccharides, it stably retains the lactic acid bacteria as well as promoting the growth.

EXAMPLE B-6

Custard Cream

One hundred parts by weight of corn starch, 100 parts by weight of a trehalose syrup obtained by the method in Example A-6, 80 parts by weight of maltose, 20 parts by weight of sucrose, and one part by weight of salt were sufficiently mixed. The mixture was admixed with 280 parts by weight of egg, and gradually mixed with 1,000 parts by weight of a boiling milk. The resultant mixture was continued stirring under heating conditions, and the heating was stopped when the corn starch in the mixture was completely gelatinized to show the whole contents semitransparent, followed by cooling the resultant and adding thereto an adequate amount of a vanilla flavor. The resultant mixture was weighed, injected and packed to obtain the desired product.

The product has a smooth surface and gloss as well as a mild taste and sweetness.

EXAMPLE B-7 l"Uiro-no-moto" (premix of sweet rice jelly)

An uiro-no-moto was prepared by homogeneously mixing 90 parts by weight of rice powder with 20 parts by weight of corn starch, 40 parts by weight of sucrose, 80 parts by weight of a massecuite-type hydrous crystalline trehalose obtained by the method in Example A-11, and 4 parts by weight of pullulan. The product was kneaded with water and an adequate amount of matcha (powdered tea), and the resultant mixture was placed in a container and steamed up for 60 min to obtain an uiro. The product has a satisfactory gloss, biting property, flavor and taste, as well as having a relatively-long shelf life because the retrogradation of the starch contained therein is well inhibited.

EXAMPLE B-8

Powdery Peptide

One part by weight of "HINUTE S", a peptide solution containing 40% edible soy beans commercialized by Fuji Oil Co., Ltd., Tokyo, Japan, was mixed with 2 parts by weight of a hydrous crystalline trehalose prepared by the method in Example A-10, and the resultant mixture was placed in a plastic vessel, dried in vacuo at 50° C., and pulverized to obtain a powdery peptide. The product having a satisfactory taste and flavor can be arbitrary used as a material for confectioneries such as premixes, sherbets and ice creams, as well as baby foods and nutrition for therapy in the form of an oral or an intubation feeding.

EXAMPLE B-9

Powdered Miso

To one part by weight of akamiso (a kind of miso) was added 3 parts by weight of a powdery anhydrous crystalline trehalose obtained by the method in Example A-4, and the mixture was poured into a metal plate having hemisphere wells on its surface and allowed to stand at ambient temperature overnight to obtain miso solids, about 4 g weight each, which were then subjected to a pulverizer to obtain the desired product.

The product can be arbitrarily used as a seasoning for instant noodles and soups, as well as a miso confectionery.

EXAMPLE B-10

Powdery Egg Yolk

Egg yolks prepared from fresh eggs were sterilized at 60°–64° C. by a plate heater, and one part by weight of the resultant liquid was mixed with 4 parts by weight of a powdery anhydrous crystalline trehalose prepared by the method in Example A-4 with respect to one part by weight of the liquid. The resultant mixture was transferred to a vessel, allowed to stand overnight to form a block while the anhydrous crystalline trehalose was allowing to convert into hydrous crystalline trehalose. The block thus obtained was pulverized by a cutter to obtain a powdery egg yolk.

The product can be arbitrarily used as a material for confectioneries for premixes, sherbets, ice creams and emulsifiers, as well as baby foods and nutrition for therapy in the form of an oral or an intubation feeding. The product can be also used as a skin refiner and hair restorer.

EXAMPLE B-11

An (beans paste)

Ten parts by weight of adzuki beans as a material was in usual manner mixed with water and boiled, followed by removing the astringency, harshness of the beans, and water-soluble impurities to obtain about 21 parts by weight of "adzuki-tsubu-nama-an". To the resultant were added 14 parts by weight of sucrose, 5 parts by weight of a trehalose syrup obtained by the method in Example A-12, and 5 parts by weight of water, and the resultant mixture was boiled, mixed with a small amount of salad oil, and carefully kneaded up so as not to paste the beans. Thus, about 35 parts by weight of the desired product was obtained.

The product is free from discoloration induced by boiling and has a satisfactory taste and flavor, and these render it useful as a material of an for bean-jam buns, buns with bean-jam filling, dumplings, bean-jam-filled wafers, sherbets and ice creams.

EXAMPLE B-12

Bread

One hundred parts by weight of wheat powder, 2 parts by weight of yeast, 5 parts by weight of sugar, one part by weight of a powdery hydrous crystalline trehalose obtained by the method in Example A-14, 0.1 part by weight of inorganic yeast food were kneaded with water in usual manner, fermented at 26° C. for 2 hours, aged for 30 min and baked up.

The product is a high-quality bread having a satisfactory hue and rising, as well as a satisfactory elasticity and mild sweetness.

EXAMPLE B-13

Ham

To one thousand parts by weight of sliced ham meat were added and ground to homogeneity 15 parts by weight of salt and 3 parts by weight of potassium nitrate, and the ham meat slices were piled up and allowed to stand overnight in a cold-storage room. Thereafter, the resultant slices were first soaked for 7 days in a cold-storage room in a salt solution consisting of 500 parts by weight of water, 100 parts by weight of salt, 3 parts by weight potassium nitrate, 40 parts by weight of a hydrous crystalline trehalose powder prepared by the method in Example A-3, and an adequate amount of a peppermint, washed with cold water in usual manner, tied up with a string, smoked, cooked, cooled and packed to obtain the desired product.

The product is a high-quality ham having a satisfactory hue, taste and flavor.

EXAMPLE B-14

Sweetened Condensed Milk

In 100 parts by weight of a fresh milk as a material were dissolved 3 parts by weight of a trehalose syrup, obtained by the method in Example A-5, and one part by weight of sucrose, and the mixture was sterilized by heating it with a plate heater, condensed into 70% syrup, d.s.b., which was then aseptically caned to obtain the desired product.

Since the product has a mild sweetness and flavor, it can be arbitrarily used as a seasoning for foods for infants and children, fruits, coffee, cocoa and tea.

EXAMPLE B-15

Cosmetic Cream

Two parts by weight of polyoxyethylene glycol monostearate, 5 parts by weight of glyceryl monostearate, self-emulsifying, 2 parts by weight of a massecuite-type high trehalose content powder obtained by the method in Example A-7, one part by weight of α-glycosyl rutin, one part by weight of liquid petrolatum, 10 parts by weight of glyceryl tri-2-ethylhexanoate, and an adequate amount of an antiseptic were in usual manner dissolved by heating. The resultant solution was admixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor under stirring conditions to obtain a cosmetic cream.

The product having a relatively-high stability can be arbitrarily used as a high-quality sunscreen, skin-refining agent and skin-whitening agent.

EXAMPLE B-16

Powdery Ginseng Extract

A half part by weight of ginseng extract was mixed with 1.5 parts by weight of an anhydrous crystalline trehalose powder prepared by the method in Example A-4, and the resultant mixture was transferred to a plain container, allowed to stand for 2 days to convert anhydrous crystalline trehalose into hydrous crystalline trehalose and to form a block, followed by pulverizing the block by a cutter and classifying the resultant into a powdery ginseng extract.

The product and adequate amounts of powdery vitamins B1 and B2 were subjected to a granulator to obtain a powdery ginseng extract containing vitamins.

The product thus obtained can be arbitrarily used as a tonic, fatigue-relieving agent and vitality-imparting agent. The product can be also used as a hair restorer.

EXAMPLE B-17

Solid Pharmaceutical

A natural human interferon-α preparation, produced by Hayashibara Biochemical Laboratories, Inc., Okayama, Japan, and commercialized by Cosmo Bio, Tokyo, Japan, was in usual manner fed to a column of an immobilized anti-human interferon-α antibody to adsorb the interferon-α, and a buffer containing calf serum albumin as a stabilizer was fed to the column, followed by removing an excessive amount of the albumin. Thereafter, the interferon-α was eluted from the column with a physiological saline containing 5% of a high trehalose content powder, prepared by the method in Example A-2, while the pH of the physiological saline was varying. The resultant eluate was membrane filtered, and the filtrate was dehydrated by the addition of about 20-fold volumes of "FINETOSE®", an anhydrous crystalline maltose powder commercialized by Hayashibara Shoji, Inc., Okayama, Japan, followed by pulverizing the resultant dehydrated product, and tabletting the resultant powder by a tabletting machine to obtain tablets containing about 150 units of the natural human interferon-α per tablet, about 200 mg weight.

The product can be orally administered as a sublingual tablet to patients at a dose of 1–10 tablets/adult/day, and arbitrarily used to treat viral diseases, allergys, rheumatisms, diabetes and malignant tumors. More particularly, the product can be suitably used as a therapeutic agent for AIDS and hepatitis, the number of patients suffering from these diseases has been remarkably increased. The trehalose and maltose incorporated in the product act as a stabilizer for the natural human interferon-α, so that the activity will be well retained for a relatively-long period of time even at ambient temperature.

EXAMPLE B-18

Sugar Coated Tablet

A crude tablet as a core, 150 mg weight, was coated with a solution consisting of 40 parts by weight of a powdery hydrous crystalline trehalose obtained by the method in Example A-3, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery hydrous crystalline trehalose, one part by weight of pullulan, and 34 parts by weight of water, and glossed with a liquid wax to obtain a sugar coated tablet having a satisfactory gloss and appearance.

The product has a relatively-high shock tolerance and retains its high quality for a relatively-long period of time.

EXAMPLE B-19

Dentifrice

A dentifrice was prepared in usual manner by mixing the following ingredients:

| | |
|---|---|
| Calcium monohydrogenphosphate | 45.0% |
| Pullulan | 2.95% |
| Sodium lauryl sulfate | 1.5% |
| Glycerine | 20.0% |
| Polyoxyethylene sorbitan laurate | 0.5% |
| Antiseptic | 0.05% |
| Powdery hydrous crystalline trehalose prepared by the method in Example A-14 | 12.0% |
| Maltitol | 5.0% |
| Water | 13.0% |

The product is satisfactorily used as a dentifrice for infants because it has an adequate sweetness.

EXAMPLE B-20

Solid Preparation for Intubation Feeding

A composition consisting of the following compositions was prepared: Five hundred parts by weight of a hydrous crystalline trehalose prepared by the method in Example A-8, 270 parts by weight of powdered egg yolk, 209 parts by weight of defatted milk, 4.4 parts by weight of sodium chloride, 1.8 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 parts by weight of nicotinamide. Twenty-five g aliquots of the composition were injected into moisture-proof laminated small bags and heat sealed to obtain the desired product.

One bag of the product is dissolved in about 150–300 ml of water into a fluid food, and orally or parenterally administered to nasal cavity, stomach or intestine by intubation feeding to supplement energy to living bodies.

EXAMPLE B-21

Hyperalimentation

A high-purity hydrous crystalline trehalose, prepared by the method in Example A-10, was dissolved in water into an about 10 w/v % aqueous trehalose solution which was then in usual manner membrane filtered to remove pyrogen, aseptically injected into a plastic bottle, and sealed to obtain the desired product.

The product, which is a satisfactorily stable hyperalimentation substantially free of change on standing, is suitable for intravenous- and intraperitoneal-administrations. A 10 w/v % solution of the product is isotonic to blood, and this means it can supplement energy to living bodies at 2-fold higher concentration than in the case of glucose.

EXAMPLE B-22

Hyperalimentation

A high-purity hydrous crystalline trehalose, prepared by the method in Example A-13, and an amino acid composition consisting of the following components were dissolved by stirring in water to give respective concentrations of 5 w/v % and 30 w/v %, and, similarly as in Example B-10 the resultant solution was purified to obtain a pyrogen-free solution, followed by injecting it into a plastic bottle and sealed to obtain the desired product.

| Components of amino acid composition | |
|---|---|
| Component | mg/100 ml |
| L-Isoleucine | 180 |
| L-Leucine | 410 |
| L-Lysine monohydrochloride | 620 |
| L-Methionine | 240 |
| L-Phenyl alanine | 290 |
| L-Threonine | 180 |
| L-Tryptophane | 60 |
| L-Valine | 200 |
| L-Arginine hydrochloride | 270 |
| L-Histidine monohydrochloride | 130 |
| Glycine | 340 |

Although the product is a multiple hyperalimentation containing trehalose and amino acids, it is satisfactorily stable without substantial change on standing and can be suitably administered intravenously and intraperitoneally to living bodies. The product can be arbitrarily used to supplement energy as well as amino acids to living bodies.

EXAMPLE B-23

Ointment for Treating Trauma

Two hundred parts by weight of a high trehalose content powder, prepared by the method in Example A-2, and 300 parts by weight of maltose were admixed with 50 parts by weight of methanol solution containing 3 parts by weight of iodine, and the resultant solution was mixed with 200 parts by weight of a 10 w/v % aqueous pullulan solution to obtain the desired product having a satisfactory extensibility and adhesiveness.

The iodine contained in the product exerts a bactericidal activity, and the trehalose in the product acts as an energy-supplementing agent on viable cells, and because of these the product shortens a healing period and satisfactorily heals a wound surface.

As is evident from above, the present novel maltose-trehalose converting enzyme converts maltose into trehalose in a satisfactorily-high yield. The present trehalose and saccharide composition containing the same obtained by the present enzymatic reaction have a relatively-high stability and quality as well as a delightful sweetness. They are assimilated, absorbed and used by living bodies as an energy source when orally administered. Therefore, they can be arbitrarily used as a sweetener, taste-improving agent, quality-improving agent, stabilizer, excipient, diluent and filler in a variety of compositions such as food products, cosmetics and pharmaceuticals.

Thus, the establishment of the present invention is to provide a novel technique to prepare trehalose from maltose which is preparable from starch as a cheap and substantially abundant natural source, and to prepare a saccharide composition containing the trehalose in an industrial-scale and a relatively-low cost. Therefore, the present invention has an unfathomably great influence on the fields such as starch-, enzyme- and biochemical-sciences, and other industrial fields, especially, food-, cosmetic- and pharmaceutical-industries, as well as forestry, fisheries, and agricultural-, livestock- and chemical-industries. Thus, the influence of the present invention on the fields is unfathomably great.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. An isolated enzyme which is obtainable from a microorganism genus selected from the group consisting of Thermus, Pimelobacter and Pseudomonas and converts maltose into trehalose and vice versa, but does not act on a system containing glucose and α-glucose 1-phosphate or β-glucose 1-phosphate, said enzyme substantially forming only trehalose and glucose when acting on maltose and substantially forming only maltose and glucose when acting on trehalose, and having the following physicochemical properties:

(1) Molecular weight About 57,000–120,000 daltons on sodium dodecylsulfate polyacrylamide gel electrophoresis (SDS-PAGE);
   (2) Isoelectric point (pI) About 3.8–5.1 on isoelectrophoresis using ampholyte; and
   (3) Inhibition of activity Inhibited by one mM $Cu^{++}$, 50 mM Tris-HCl buffer.

2. The enzyme in accordance with claim 1, wherein said microorganism is Pimelobacter sp. R48 (FERM BP-4315), *Pseudomonas putida* H262 (FERM BP-4579) or *Thermus aquaticus* (ATCC 33923).

3. The enzyme in accordance with claim 1, which has a partial amino acid sequence selected from the group consisting of:

(1) Trp-$X_1$-Arg-$X_2$-Ala-$X_3$-Phe (SEQ ID NO: 4) (where "$X_1$" means "Phe" or "Pro"; "$X_2$", "Thr" or "Pro"; and "$X_3$", "Val" or "Ala"); and
   (2) Ala-Val-$X_4$-Tyr (SEQ ID NO: 5) (where "$X_4$" means "Phe" or "Ile").

4. The enzyme in accordance with claim 1, wherein said microorganism is a microorganism of the genus Thermus selected from the group consisting of the species *Thermus aquaticus* (ATCC 25104), *Thermus aquaticus* (ATCC 33923), *Thermus filiformis* (ATCC 43280), *Thermus ruber* (ATCC 35948), Thermus sp. (ATCC 43814), and Thermus sp. (ATCC 43815).

* * * * *